United States Patent
Scott et al.

(10) Patent No.: US 10,633,493 B2
(45) Date of Patent: Apr. 28, 2020

(54) FACILE ASSEMBLY OF SOFT NANOARCHITECTURES AND CO-LOADING OF HYDROPHILIC AND HYDROPHOBIC MOLECULES VIA FLASH NANOPRECIPITATION

(71) Applicant: Northwestern University, Evanston, IL (US)

(72) Inventors: Evan A. Scott, Chicago, IL (US); Sean D. Allen, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 15/656,905

(22) Filed: Jul. 21, 2017

(65) Prior Publication Data

US 2018/0022878 A1    Jan. 25, 2018

Related U.S. Application Data

(60) Provisional application No. 62/365,849, filed on Jul. 22, 2016.

(51) Int. Cl.

| | |
|---|---|
| A61K 31/352 | (2006.01) |
| A61K 31/365 | (2006.01) |
| A61K 9/107 | (2006.01) |
| A61K 9/127 | (2006.01) |
| C08J 3/14 | (2006.01) |
| A61K 47/34 | (2017.01) |
| A61K 47/36 | (2006.01) |
| A61K 31/436 | (2006.01) |
| A61K 49/00 | (2006.01) |
| A61K 9/00 | (2006.01) |
| A61K 38/46 | (2006.01) |
| C12N 15/113 | (2010.01) |
| B01F 3/08 | (2006.01) |
| B01F 5/02 | (2006.01) |
| B01F 13/00 | (2006.01) |

(52) U.S. Cl.
CPC .............. *C08J 3/14* (2013.01); *A61K 9/0019* (2013.01); *A61K 9/107* (2013.01); *A61K 9/1273* (2013.01); *A61K 31/352* (2013.01); *A61K 31/365* (2013.01); *A61K 31/436* (2013.01); *A61K 38/465* (2013.01); *A61K 47/34* (2013.01); *A61K 47/36* (2013.01); *A61K 49/0047* (2013.01); *A61K 49/0054* (2013.01); *A61K 49/0065* (2013.01); *B01F 3/0807* (2013.01); *B01F 3/0861* (2013.01); *B01F 5/02* (2013.01); *B01F 5/0256* (2013.01); *B01F 13/0059* (2013.01); *C12N 15/113* (2013.01); *C12Y 301/03001* (2013.01); *C08J 2371/02* (2013.01); *C08J 2381/02* (2013.01); *C08J 2381/04* (2013.01); *C12N 2310/14* (2013.01); *C12N 2320/32* (2013.01)

(58) Field of Classification Search
CPC .... A61K 31/352; A61K 31/436; A61K 47/34; A61K 47/36; A61K 9/107
See application file for complete search history.

(56) References Cited

U.S. PATENT DOCUMENTS

| | | |
|---|---|---|
| 8,137,699 B2 | 3/2012 | Johnson et al. |
| 2012/0171254 A1 | 7/2012 | Johnson et al. |

OTHER PUBLICATIONS

Akbulut et al. Generic Method of Preparing Multifunctional Fluorescent Nanoparticles Using Flash NanoPrecipitation, Adv. Funct. Mater. 19(5) (2009) 718-725.
Allen et al. Engineering nanomaterials to address cell-mediated inflammation in atherosclerosis, Regen Eng Transl Med 2(1) (2016) 37-50.
Battaglia et al. Rapamycin selectively expands CD4+CD25+ FoxP3+ regulatory T cells, Blood 105(12) (2005) 4743-8.
Bleul et al. Techniques to Control Polymersome Size, Macromolecules 48(20) (2015) 7396-7409.
Cao et al. Toll-like receptor-mediated induction of type I interferon in plasmacytoid dendritic cells requires the rapamycin-sensitive PI(3)K-mTOR-p70S6K pathway, Nat Immunol 9(10) (2008) 1157-64.
Cerritelli et al. Aggregation Behavior of Poly(ethylene glycol-bl-propylene sulfide) Di- and Triblock Copolymers in Aqueous Solution, Langmuir 25(19) (2009) 11328-11335.
Cerritelli et al. Thermodynamic and kinetic effects in the aggregation behavior of a poly(ethylene glycol-b-propylene sulfide-b-ethylene glycol) ABA triblock copolymer, Macromolecules 38(18) (2005) 7845-7851.
Cheng et al. A competitive aggregation model for Flash NanoPrecipitation, J. Colloid Interface Sci. 351(2) (2010) 330-342.
Choi et al. Mechanism for the endocytosis of spherical nucleic acid nanoparticle conjugates, Proc Natl Acad Sci U S A 110(19) (2013) 7625-30.
Coenen et al. Rapamycin, not cyclosporine, permits thymic generation and peripheral preservation of CD4+ CD25+ FoxP3+ T cells, Bone Marrow Transplant 39(9) (2007) 537-45.
Cui et al. Shear flow controlled morphological polydispersity of amphiphilic ABA triblock copolymer vesicles, Langmuir 29(50) (2013) 15704-10.
Dionzou et al. M. Comparison of methods for the fabrication and the characterization of polymer self-assemblies: what are the important parameters?, Soft Matter 12(7) (2016) 2166-76.
Discher et al. Polymersomes: tough vesicles made from diblock copolymers, Science 284(5417) (1999) 1143-6.
Dowling et al. TLR8 agonist encapsulating polymersomes mimic the immunomodulating effect of the live BCG vaccine on neonatal dendritic cells while dramatically enhancing IL-12p70 production, Journal of Clinical Investigation in Press (2017).

(Continued)

*Primary Examiner* — Zohreh A Fay
(74) *Attorney, Agent, or Firm* — Quarles & Brady LLP

(57) ABSTRACT

Described herein are flash nanoprecipitation methods capable of encapsulating hydrophobic molecules, hydrophilic molecules, bioactive protein therapeutics, or other target molecules in amphiphilic copolymer nanocarriers.

24 Claims, 16 Drawing Sheets

(Continued)

(6 of 16 Drawing Sheet(s) Filed in Color)

(56) References Cited

OTHER PUBLICATIONS

Duan, et al. Physicochemical Characteristics of Nanoparticles Affect Circulation, Biodistribution, Cellular Internalization, and Trafficking, Small 9(9-10) (2013) 1521-1532.
Gao et al. Contrasting effects of cyclosporine and rapamycin in de novo generation of alloantigen-specific regulatory T cells, Am J Transplant 7(7) (2007) 1722-32.
Geng et al. Shape effects of filaments versus spherical particles in flow and drug delivery, Nat Nanotechnol 2(4) (2007) 249-55.
Grumelard et al. Soft nanotubes from amphiphilic ABA triblock macromonomers, Chem Commun (Camb) (13) (2004)1462-3.
Haddadi et al. Delivery of rapamycin by PLGA nanoparticles enhances its suppressive activity on dendritic cells, J Biomed Mater Res A 84(4) (2008) 885-98.
Hammer et al. Towards an artificial cell, FEBS Lett. 586(18) (2012) 2882-2890.
Han et al. A simple confined impingement jets mixer for flash nanoprecipitation, J. Pharm. Sci. 101(10) (2012) 4018-23.
Horwitz et al. Substrates for cytochemical demonstration of enzyme activity. II. Some dihalo-3-indolyl phosphates and sulfates, J. Med. Chem. 9(3) (1966) 447.
Ikonen et al. Efficacies of sirolimus (rapamycin) and cyclosporine in allograft vascular disease in non-human primates: trough levels of sirolimus correlate with inhibition of progression of arterial intimal thickening, Transpl Int 13 Suppl 1 (2000) S314-20.
Jeon et al. Protein Surface Interactions in the Presence of Polyethylene Oxide .1. Simplified Theory, J. Colloid Interface Sci. 142(1) (1991) 149-158.
Jhunjhunwala et al. Delivery of rapamycin to dendritic cells using degradable microparticles, J Control Release 133(3) (2009) 191-7.
Johnson et al. Flash NanoPrecipitation of organic actives and block copolymers using a confined impinging jets mixer, Aust. J. Chem. 56(10) (2003) 1021-1024.
Johnson et al. Mechanism for rapid self-assembly of block copolymer nanoparticles, Phys. Rev. Lett. 91(11) (2003) 118302.
Johnson et al. Chemical processing and micromixing in confined impinging jets. AIChE J., 49:2264-2282.
Kim et al. Polymersome stomatocytes: controlled shape transformation in polymer vesicles, J. Am. Chem. Soc. 132 (36) (2010) 12522-4.
Kumar et al. Nanoparticle stability: Processing pathways for solvent removal, Chem. Eng. Sci. 64(6) (2009) 1358-1361.
Kumar et al. Formulation and stability of itraconazole and odanacatib nanoparticles: governing physical parameters, Mol Pharm 6(4) (2009) 1118-24.
La et al. Colloidal inverse bicontinuous cubic membranes of block copolymers with tunable surface functional groups, Nat Chem 6(6) (2014) 534-41.
Le Meins et al. Recent trends in the tuning of polymersomes' membrane properties, Eur Phys J E Soft Matter 34(2) (2011)14.
Li al. Temporal regulation of rapamycin on memory CTL programming by IL-12, PloS one 6(9) (2011) e25177.
Lipowsky, R. The morphology of lipid membranes, Curr Opin Struct Biol 5(4) (1995) 531-40.
Liu et al. Fluoxetine regulates mTOR signalling in a region-dependent manner in depression-like mice, Scientific reports 5 (2015) 16024.
Lobling et al. Rational design of ABC triblock terpolymer solution nanostructures with controlled patch morphology, Nat Commun 7 (2016) 12097.
Lutz et al. An advanced culture method for generating large quantities of highly pure dendritic cells from mouse bone marrow, J Immunol Methods 223(1) (1999) 77-92.
Maherani et al. Calcein release behavior from liposomal bilayer; influence of physicochemical/mechanical/structural properties of lipids, Biochimie 95(11) (2013) 2018-33.
Mai et al. Self-assembly of block copolymers, Chem. Soc. Rev. 41(18) (2012) 5969-85.
Massignani et al. Enhanced fluorescence imaging of live cells by effective cytosolic delivery of probes, PLoS One 5 (5) (2010) e10459.
Mckenzie et al. Bicontinuous Nanospheres from Simple Amorphous Amphiphilic Diblock Copolymers, Macromolecules 46(24) (2013) 9845-9848.
Mercalli et al. Rapamycin unbalances the polarization of human macrophages to M1, Immunology 140(2) (2013) 179-90.
Napoli et al. Oxidation-responsive polymeric vesicles, Nat. Mater. 3(3) (2004) 183-9.
Nichols et al. Factors affecting size and swelling of poly(ethylene glycol) microspheres formed in aqueous sodium sulfate solutions without surfactants, Biomaterials 30(29) (2009) 5283-91.
Nicol et al. Dynamics of poly(propylene sulfide) studied by dynamic mechanical measurements and dielectric spectroscopy, Macromolecules 32(22) (1999) 7530-7536.
Nikoubashman et al. Directed assembly of soft colloids through rapid solvent exchange. ACS Nano. 2016; 10:1425-1433.
Noris et al. Regulatory T cells and T cell depletion: role of immunosuppressive drugs, J Am Soc Nephrol 18(3) (2007) 1007-18.
O'Neil et al. A Novel Method for the Encapsulation of Biomolecules into Polymersomes via Direct Hydration, Langmuir 25(16) (2009) 9025-9029.
Pessi et al. Microfluidics-assisted engineering of polymeric microcapsules with high encapsulation efficiency for protein drug delivery, Int. J. Pharm. 472(1-2) (2014) 82-87.
Pinkerton et al. Formation of stable nanocarriers by in situ ion pairing during block-copolymer-directed rapid precipitation, Mol Pharm 10(1) (2013) 319-28.
Poston et al. Rapamycin reverses chronic graft vascular disease in a novel cardiac allograft model, Circulation 100 (1) (1999) 67-74.
Pustulka et al. Flash nanoprecipitation: particle structure and stability, Mol Pharm 10(11) (2013) 4367-77.
Qu et al. The effect of immunosuppressive drug rapamycin on regulatory CD4+CD25+Foxp3+T cells in mice, Transpl Immunol 17(3) (2007) 153-61.
Rikken et al. Probing morphological changes in polymersomes with magnetic birefringence, Chem Commun (Camb) 50(40) (2014) 5394-6.
Rikken et al. Shaping polymersomes into predictable morphologies via out-of-equilibrium self-assembly, Nat Commun 7 (2016) 12606.
Robertson et al. pH-sensitive tubular polymersomes: formation and applications in cellular delivery, ACS Nano 8(5) (2014)4650-61.
Saad et al. Principles of nanoparticle formation by flash nanoprecipitation, Nano Today 11(2) (2016) 212-227.
Saito et al. Multicompartment Micelles from Polyester-Containing ABC Miktoarm Star Terpolymers, Macromolecules 41(22) (2008) 8815-8822.
Salva et al. Polymersome shape transformation at the nanoscale, ACS Nano 7(10) (2013) 9298-311.
Scott et al. Dendritic cell activation and T cell priming with adjuvant- and antigen-loaded oxidation-sensitive polymersomes, Biomaterials 33(26) (2012) 6211-9.
Scott et al. Modular scaffolds assembled around living cells using poly(ethylene glycol) microspheres with Macroporation via a non-cytotoxic porogen, Acta Biomater 6(1) (2010) 29-38.
Segura et al. Synthesis and in vitro characterization of an ABC triblock copolymer for siRNA delivery, Bioconjugate Chem. 18(3) (2007) 736-745.
Shillcock et al. Spontaneous vesicle self-assembly: a mesoscopic view of membrane dynamics, Langmuir 28(1) (2012) 541-7.
Shum et al. Microfluidic fabrication of monodisperse biocompatible and biodegradable polymersomes with controlled permeability, J. Am. Chem. Soc. 130(29) (2008) 9543-9.
Soo et al. Preparation of block copolymer vesicles in solution, J Polym Sci Pol Phys 42(6) (2004) 923-938.

(56) References Cited

OTHER PUBLICATIONS

Sterling et al. Zinc 15—Ligand Discovery for Everyone, J Chem Inf Model 55(11) (2015) 2324-37.
Stoica et al. Selective pharmacogenetic inhibition of mammalian target of Rapamycin complex I (mTORC1) blocks long-term synaptic plasticity and memory storage, Proceedings of the National Academy of Sciences of the United States of America 108(9) (2011) 3791-6.
Stano et al. Tunable T cell immunity towards a protein antigen using polymersomes vs. solid-core nanoparticles, Biomaterials 34(17) (2013) 4339-46.
Stewart et al. Block Copolymer Nanotubes, Angew. Chem. Int. Ed. Engl. 39(2) (2000) 340-344.
Tang et al. Polymer directed self-assembly of pH-responsive antioxidant nanopartides, Langmuir 31(12) (2015) 3612-20.
Thiermann et al. Size controlled polymersomes by continuous self-assembly in micromixers, Polymer 53(11) (2012) 2205-2210.
Thomson et al. Immunoregulatory functions of mTOR inhibition, Nat Rev Immunol 9(5) (2009) 324-37.
Turnquist et al. Rapamycin-conditioned dendritic cells are poor stimulators of allogeneic CD4+ T cells, but enrich for antigen-specific Foxp3+ T regulatory cells and promote organ transplant tolerance, J Immunol 178(11) (2007) 7018-31.
Van Oers et al. Tubular polymersomes: a cross-linker-induced shape transformation, J. Am. Chem. Soc. 135(44) (2013) 16308-11.
Vasdekis et al. Vesicle Photonics, Annu. Rev. Mater. Res. 43 (2013)283-305.
Vasdekis et al. Precision intracellular delivery based on optofluidic polymersome rupture, ACS Nano 6(9) (2012) 7850-7.
Wang et al. Cellular uptake of nanoparticles by membrane penetration: a study combining confocal microscopy with FTIR spectroelectrochemistry, ACS Nano 6(2) (2012) 1251-9.
Wohl et al. Silicate esters of paclitaxel and docetaxel: synthesis, hydrophobicity, hydrolytic stability, cytotoxicity, and prodrug potential, J. Med. Chem. 57(6) (2014) 2368-79.
Xiong et al. Flt3L combined with rapamycin promotes cardiac allograft tolerance by inducing regulatory dendritic cells and allograft autophagy in mice, PloS one 7(10) (2012) e46230.
YABU Creation of Functional and Structured Polymer Particles by Self-Organized Precipitation (SORP), Bull. Chem. Soc. Jpn. 85(3) (2012) 265-274.
Yi et al. Tailoring Nanostructure Morphology for Enhanced Targeting of Dendritic Cells in Atherosclerosis, ACS Nano 10(12) (2016) 11290-11303.
Zhu, Z. Flash nanoprecipitation: prediction and enhancement of particle stability via drug structure, Mol Pharm 11(3) (2014) 776-86.

FACILE ASSEMBLY OF SOFT NANOARCHITECTURES AND CO-LOADING OF HYDROPHILIC AND HYDROPHOBIC MOLECULES VIA FLASH NANOPRECIPITATION

CROSS-REFERENCE TO RELATED APPLICATIONS

This application claims priority to U.S. Provisional Application No. 62/365,849, filed Jul. 22, 2016, which is incorporated herein.

STATEMENT REGARDING FEDERALLY SPONSORED RESEARCH

This invention was made with government support under CBET1453576 awarded by the National Science Foundation. The government has certain rights in the invention.

BACKGROUND

Nanocarriers present a versatile method of controlled delivery for bioactive molecules that may otherwise be too hydrophobic or susceptible to degradation for therapeutic applications. A key parameter of nanocarrier design is the nanoarchitecture, which strongly influences in vivo transport, biodistribution, and cellular uptake. The ability to tailor nanocarrier architecture has resulted in numerous advancements in targeted delivery, for example, providing enhanced circulation time, membrane permeation and the simultaneous loading of multiple molecules that differ in water solubility. The self-assembly of block-copolymers allows the formation of diverse soft nanoarchitectures, but presents several engineering challenges, namely: loading efficiency, scalability, repeatability and ease of fabrication, among others. Flash nanoprecipitation (FNP) is a fabrication technique capable of addressing the majority of these issues, but has so far only been applied for the formation of solid-core nanoparticles and their loading with hydrophobic drugs.

SUMMARY OF THE INVENTION

In a first aspect, provided herein is a method for preparing nanocarriers by flash precipitation comprising the steps of: (i) providing an organic phase solution comprising an amphiphilic copolymer and a process solvent, wherein the amphiphilic copolymer has a glass transition temperature below 0° C., (ii) providing an aqueous phase solution comprising an aqueous solvent, (iii) mixing the organic phase solution and the aqueous phase solution to form a mixture, and (iv) introducing the mixture into a reservoir to cause precipitation of the amphiphilic copolymer as a nanocarrier. In some embodiments, the process solvent is selected from the group consisting of tetrahydrofuran (THF), dimethylformamide (DMF), and dimethyl sulfoxide (DMSO). In some embodiments, the aqueous solvent is water.

In some embodiments, the amphiphilic copolymer has a glass transition temperature between about −40° C. and about 0° C. In some embodiments, the amphiphilic copolymer is poly(ethylene glycol)-bl-poly(propylene sulfide) (PEG-bl-PPS). In one embodiment, the copolymer is $PEG_{17}$-bl-$PPS_{30}$-Thiol.

In some embodiments, the organic phase solution additionally comprises one or more target molecules. In some embodiments, the aqueous phase solution additionally comprises a target molecule. In some embodiments, the target molecule is selected from the group consisting of a DNA molecule, an RNA molecule, a plasmid, a peptide, a protein, and combinations thereof.

In some embodiments, the reservoir comprises an aqueous nonsolvent. In some embodiments, the reservoir comprises a target molecule.

In some embodiments, the mixing is by impingement. In some embodiments, the mixing comprises at least 2 impingements.

In a second aspect, provided herein is a method for preparing nanocarriers by flash precipitation comprising the steps of: (i) providing an organic phase solution comprising an amphiphilic copolymer and a process solvent, wherein the amphiphilic copolymer has a glass transition temperature below 0° C., (ii) providing an aqueous phase solution comprising an aqueous solvent and an target molecule, (iii) mixing the organic phase solution and the aqueous phase solution to form a mixture, and (iv) introducing the mixture into a reservoir to cause precipitation of the amphiphilic copolymer as a nanocarrier loaded with the target molecule.

In some embodiments, the target molecule is selected from the group consisting of a DNA molecule, an RNA molecule, a plasmid, a peptide, a protein, and combinations thereof.

In some embodiments, the process solvent is selected from the group consisting of tetrahydrofuran (THF), dimethylformamide (DMF), and dimethyl sulfoxide (DMSO).

In some embodiments of the second aspect, the aqueous solvent is water. In some embodiments, the amphiphilic copolymer has a glass transition temperature between about −40° C. and about 0° C. In some embodiments, the amphiphilic copolymer is poly(ethylene glycol)-bl-poly(propylene sulfide) (PEG-bl-PPS). In one embodiment, the copolymer is $PEG_{17}$-bl-$PPS_{30}$-Thiol.

In some embodiments of the second aspect, the organic phase solution additionally comprises an target molecule.

In a third aspect, provided herein is a method for preparing nanocarriers by flash precipitation comprising the steps of: (i) providing an organic phase solution comprising an amphiphilic copolymer and a process solvent, wherein the amphiphilic copolymer has a glass transition temperature below 0° C., (ii) providing an aqueous phase solution comprising an aqueous solvent and an target molecule, (iii) mixing the organic phase solution and the first aqueous phase solution to form a mixture, (iii) portioning the mixture into a first portion and a second portion, (iv) mixing the first portion and the second portion to form a second mixture, and (v) introducing the second mixture into a reservoir to cause precipitation of the amphiphilic copolymer as a nanocarrier loaded with the target molecule. In some embodiments, steps (iii) and (iv) are repeated at least one time.

In some embodiments of the third aspect, the organic phase solution additionally comprises a second target molecule.

In some embodiments, the mixing is by impingement.

In a fourth aspect, provided herein is a nanocarrier made by any of the methods described herein.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 1A shows a schematic of the CIJ mixer. FIG. 1B shows the structure of the diblock copolymer poly(ethylene glycol)-block-poly (propylene sulfide), and the weight fraction (fPEG) dependent nanostructure known to form using the thin film hydration method. FIG. 1C shows a representative cryoTEM image of polymersomes formed by FNP, scale bar+300 nm. Insert is a size distribution of polymersomes measured by nanoparticle tracking analysis (NTA), n=6. Standard deviation is represented by the dotted lines.

FIG. 2A shows DLS mean diameter of polymersomes formed after multiple inpingements (1×-5×), or formed by thin film (TF) or solvent dispersion (SD) with (E) or without (NE) extrusion. Error bars are standard error, n=5. FIG. 2B shows DLS distribution of 5× impinged polymersomes the day of formation or after four days of storage at room temperature. Error bars are standard error, n=3. FIGS. 2C-2G show CryoTEM images of polymersomes formed after multiple impingements (1×-5×, respectively) with inserts of DLS size distributions. X- and y-axes correspond to that of FIG. 2B.

FIG. 3A shows diameter of nanostructures formed via FNP from PEG-bl-PPS copolymers of varying block lengths. Error bars represent the standard deviation of the nanostructure populations (PdI×Mean Diameter). Dotted area represents polymersomes-forming samples. Arrows point out samples of note. †Samples formed using DMF as the organic solvent, rather than THF. ‡Sample formed using water instead of 1×PBS. FIGS. 3B-3G show weight fractions of PEG responsible for forming specific nanostructures via flash nanoprecipitation, paired with cartoon and representative cryoTEM images. All scale bars=100 nm, with the exception of scale bars within FIGS. 3B and 3E, which are 300 nm. Sample number is listed in the upper corner of each cryoTEM image, and the number of impingements used is listed for each morphology. See Table 1 for details of the copolymers and FIGS. 10A-10E for low magnification images.

FIG. 5A shows the percentage of CD8+ T cells (CD45+ CD3+ CD4−CD8+) and CD4+ T cells (CD45+ CD3+ CD4+ CD8−) within the total T cell population (CD45+ CD3+) and percentage of CD8+ DCs (CD11c+I-A/I-E+ CD8+) within the total DC (CD11c+) population. Treatment groups were rapamycin polymersomes (R-PS), free rapamycin, blank polymersomes, and vehicle (PBS). FIG. 5B shows T cell subpopulations as a percent of total T cell population for all four treatment groups. FIG. 5C shows T cells in the spleen and lymph nodes, as a percentage of CD45+ cells. FIG. 5D shows median fluorescence intensity of the polymersome channel for selected cell populations in the spleen and lymph nodes of mice administered rapamycin/DiD-loaded polymersomes. N=3, statistical significance determined by Tukey's multiple comparison test, * $p<0.05$,  $p<0.01$, * $p<0.001$, **** $p<0.0001$.

INCORPORATION BY REFERENCE

All publications, including but not limited to patents and patent applications, cited in this specification are herein incorporated by reference as though set forth in their entirety in the present application.

DETAILED DESCRIPTION OF THE INVENTION

Described herein are flash nanoprecipitation preparation methods for the preparation of nanocarriers. The methods described herein assemble and load nanocarriers with therapeutic molecules by flash nanoprecipitation.

Figures 1A, 1B, 1C:
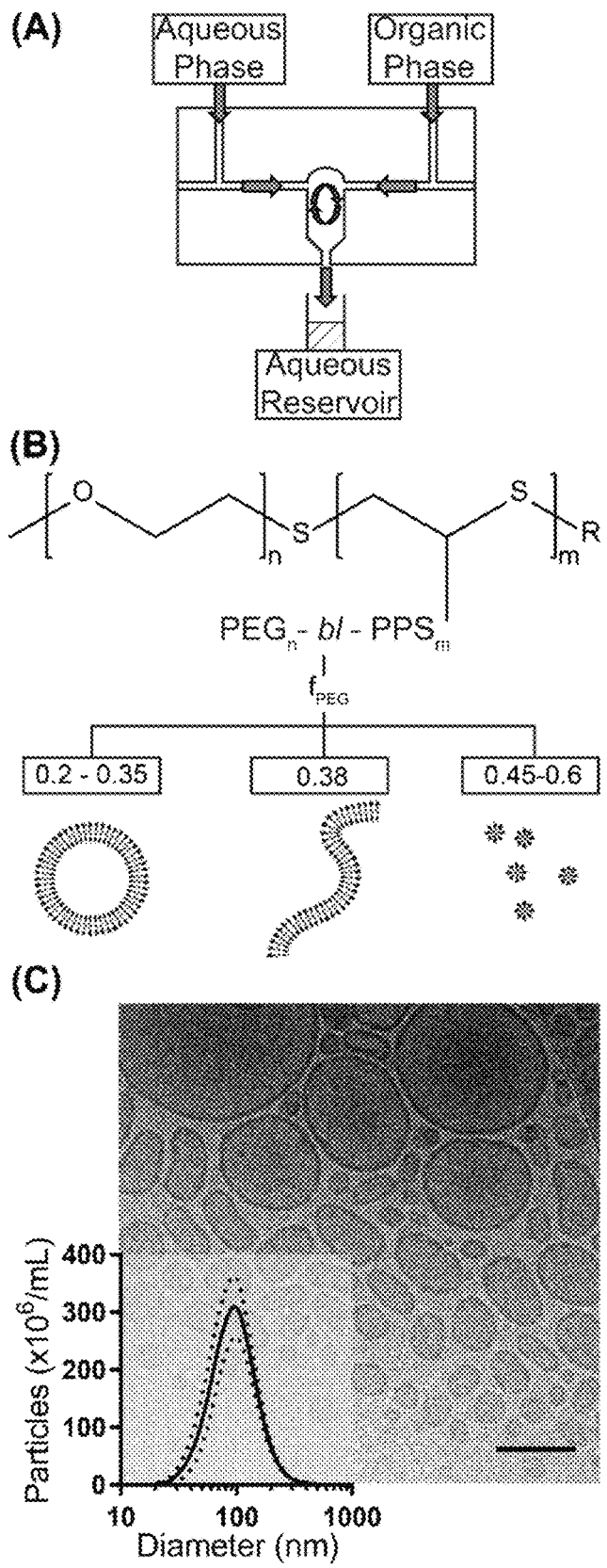
FIGS. 1A-1C show an overview of polymersome formation by flash nanoprecipitation (FNP).

As used herein, "flash nanoprecipitation" (FNP) refers to a process in which a block copolymer is assembled into a nanocarrier architecture. FNP is also used to load the nanocarrier with a target molecule such as a therapeutic or diagnostic molecule. FNP methods of the present invention employ multi-stream mixers in which an organic solution and a block copolymer dissolved in a suitable solvent are impinged upon an aqueous solution under turbulent conditions and subsequently introduced into an aqueous reservoir (FIG. 1A). The supersaturated conditions generated by the turbulent mixing induces precipitation of the block copolymer for stabilization of monodisperse nanoparticles which may be loaded with one or more target molecules. Mixing occurs over millisecond timescales and is followed by transfer to a reservoir comprising a second aqueous solution to strip away solvent still associating with the aggregated block copolymer. Similar FNP methods are known in the art (U.S. Pat. No. 8,137,699 and U.S. Patent Publication No. 2012/0171254, each of which is incorporated herein in its entirety), however the methods of embodiments of the present invention offer at least the advantages of being capable of loading hydrophilic target molecules, such as, but not limited to, large hydrophilic macromolecules such as RNA, DNA and proteins, and creating more advanced nanocarrier architectures with high loading efficiency.

Nanocarriers can be produced from amphiphilic copolymers that are dissolved in a process solvent. After the amphiphilic copolymers are dissolved in the process solvent, thereby forming an organic phase solution, the solution is rapidly mixed with a first aqueous solution and nanocarriers are flash precipitated following introduction of the mixture into a reservoir comprising a second aqueous solution. This mixing can be achieved through various methods during which the mixing velocity, number of impingements, temperature and reservoir volume are controlled. In addition, a target molecule can be added with the amphiphilic copolymer in the process solvent prior to mixing, or a target molecule can be added to the first aqueous solution prior to mixing. It is also envisioned that one or more target molecules can be added to both the process solvent and the aqueous solution resulting in the loading of multiple target molecules into the nanocarrier architecture.

Nanocarriers formed by the methods of the present invention are characterized by complex or vesicular nanoarchitectures capable of encapsulating or comprising as part of the nanocarrier a target molecule. Nanoarchitectures formed by the methods of embodiments of the present invention are bicontinuous and may be characterized as, for example, nanospheres, filomicelles, cubisomes, vesicles, tubules, nested vesicles, filiments, and vesicular, multilamellar and tubular polymersomes. It is envisioned that any soft nanoarchitecture with an internal chamber capable of encapsulating a target molecule may be formed by the methods of embodiments of the present invention. One of skill in the art will appreciate that changes in the amphiphilic copolymer, the mixing velocity, number of impingements, temperature and reservoir volume will impact the nanoarchitecture of the nanocarrier produced by the methods of the present invention.

Polymersomes are comprised of three separate topological regions: an inner aqueous cavity, a hydrophobic membrane, and an external surface, that together allow for simultaneous or individual transport of both water soluble/hydrophobic and lipophilic/hydrophobic target molecules. Polymersomes may be vesicular, multilamellar or tubular. Polymersomes formed by the methods of embodiments of the present invention have a polydispersity index (PDI) of between about 0.01 and about 0.99. In some embodiments, the PDI is between 0.20 and 0.64. In one embodiment, the PDI is less than 0.15 and the polymersomes are monodisperse.

In the methods according to embodiments of the present invention, mixing of the organic phase solution and the aqueous solution occurs by impingement mixing or turbulent mixing. Mixing may occur in the present methods any number of times (i.e., 1, 2, 3, 4, 5, 6, 7, 8, 9, 10, 10+, 100+, 1000+, 10,000+ times or more) before the mixture is introduced to the second aqueous phase solution. In embodiments of the method in which the mixing occurs two or more times, following the first mixing, the mixture is separated into a first portion and a second portion and the two portions are impinged upon one another or mixed using the same means as for the first mixing. The portioning and mixing steps may be repeated until the solutions have been mixed the desired number of times. In some embodiments, the solutions are mixed 2 times. In some embodiments, the solutions are mixed 3 times. In some embodiments, the solutions are mixed 5 times. In some embodiments, the solutions are mixed 10 or more times. In some embodiments, the solutions are mixed 100 or more times.

Without being bound to any particular theory, it is believed that the number of impingements effects the nanoarchitecture of the nanocarrier produced by the methods of the present invention. Multiple impingements have shown to both decrease the mean polymersome diameter and lower the PDI to levels equivalent to those achievable by extrusion methods for polymersome preparation. In some embodiments, the solutions are impinged about 2 to 3 times and form tubule nanoarchitectures. In some embodiments, the solutions are mixed about 3 to 4 times and form nested vesicle nanoarchitectures. In some embodiments, the solutions are mixed about 4 or more times and form monodisperse polymersomes. In some embodiments, the solutions are mixed a sufficient number of times such that the resulting polymersomes are monodisperse. It is envisioned that the number of impingements may vary depending on the modification of other variables.

Any impingement mixer or turbulent known in the art can be used in the methods of the present invention. It is minimally required that 2 liquids are mixed under turbulent conditions, such as a mixer in which 2 or more liquids flow to meet at a single point. A suitable mixer for use in the methods of the present invention may include one or more inlets in which the two solutions are introduced into the mixing vessel through independent inlet tubes. A suitable mixer may also include temperature controlling elements to adjust or maintain the mixing at a suitable temperature. A suitable temperature will be a temperature at which all components are stable, such as, for example, a temperate at which any included protein will remain folded and will not denature. In some embodiments the temperature is between 0° C. and 40° C. In some embodiments the temperature is between 4° C. and 37° C. For volatile organic solvents the temperature range is below their boiling point. It is envisioned that higher temperatures may be used with polymers. Any mixer capable of providing a sufficient mixing velocity with controlled introduction of the organic phase solution and the first aqueous phase solution could facilitate flash precipitation under the methods of the present invention. Examples of suitable mixers include, but are not limited to, confined impingement jets mixers, impinging get mixers, T-jet mixers, opposed jet mixers, micromixers, and the like.

A sufficient mixing velocity or flow rate is considered to be a velocity at which turbulent mixing is achieved. Variables including fluid density, channel length and fluid viscosity will change based on the solvent, polymer, mixer, and any target molecules present and will change the mixing velocity necessary to achieve turbulent mixing. In some embodiments, turbulent mixing will be achieved at a Reynold (RE) number greater than 4000 based on the following equation. In some embodiments, turbulent mixing at an RE greater than 4000 is ideal, but transitional flows with an RE between 1000 to 4000 will be sufficient to induce flash nanoprecipitation formation of nanocarriers.

$$RE = \frac{\text{(fluid density)(mixing velocity)(channel length)}}{\text{(fluid viscosity)}}$$

A suitable temperature will be a temperature at which all components are stable, such as, for example, a temperate at which any included protein will remain folded and will not denature. In some embodiments the temperature is between 0° C. and 40° C. In some embodiments the temperature is between 4° C. and 37° C.

The reservoir volume used in embodiments of the methods of the present invention is sufficiently high such that the process solvent is rapidly stripped away from the amphiphilic copolymer causing precipitation and formation of nanocarriers. In some embodiments of the invention the reservoir-to-process solvent volume ratio is at least about 5:1 (i.e., 5:1, 6:1, 7:1, 8:1, 10:1, 12:1, 15:1, 18:1, 20:1, 25:1 or about 30:1). In some embodiments, the reservoir-to-process solvent volume ratio is greater than 6:1. In some embodiments reservoir-to-process solvent volume ratio is between about 6:1 and about 20:1. In one embodiment, the reservoir-to-process solvent volume ratio is less than 20:1, preferably less than 10:1. In one embodiment, the reservoir-to-process solvent volume ratio is 6:1. The reservoir comprises an aqueous nonsolvent solution in which the polymer process solvent is miscible, but in which the hydrophobic blocks of the copolymer are insoluble. In some embodiments of the invention, the reservoir comprises a target molecule to be loaded upon flash precipitation of the nanocarrier. Without being bound by any particular theory, it is believed that upon introduction of the process solvent into the aqueous solution of the reservoir, the process solvent will disperse as it is miscible with water, but the insoluble hydrophobic blocks of the copolymer will aggregate. The aggregation of the hydrophobic blocks of the copolymer will be controlled to some extent by the presence of the hydrophilic blocks of the copolymer which are soluble in the aqueous nonsolvent solution.

As used herein, the term "organic phase solution," refers collectively to the solution comprising the process solvent, the amphiphilic copolymer, and optionally one or more target molecules. The process solvent may be any water miscible organic solvent in which the hydrophobic block of the amphiphilic copolymer is soluble. The proper process solvent will be selected based on the identity and characteristics of the amphiphilic copolymer selected. Water miscible organic solvents are known in the art and include, without limitation, tetrahydrofuran (THF), dimethylformamide (DMF), dimethyl sulfoxide (DMSO), acetonitrile, methanol, 1,2-Butanediol, 1,3-Butanediol, 1,3-Propanediol, 1,4-Butanediol, 1,4-Dioxane, 1,5-Pentanediol, 1-Propanol, 2-Butoxyethanol, 2-Propanol, acetaldehyde, acetic acid, acetone, butyric acid, diethanolamine, diethylenetriamine, dimethoxyethane, dimethyl sulfoxide, dimethylformamide, ethanol, ethylamine, ethylene glycol, formic acid, furfuryl alcohol, glycerol, methyl diethanolamine, methyl isocyanide, propanoic acid, propylene glycol, pyridine, tetrahydrofuran, triethylene, and glycol. The organic phase solution may optionally comprise one or more lipophilic or hydrophobic target molecules. In one embodiment, the process solvent is THF. In one embodiment, the process solvent is DMSO. In one embodiment, the process solvent is DMF.

Figures 3A, 3B, 3C, 3D, 3E, 3F, 3G:
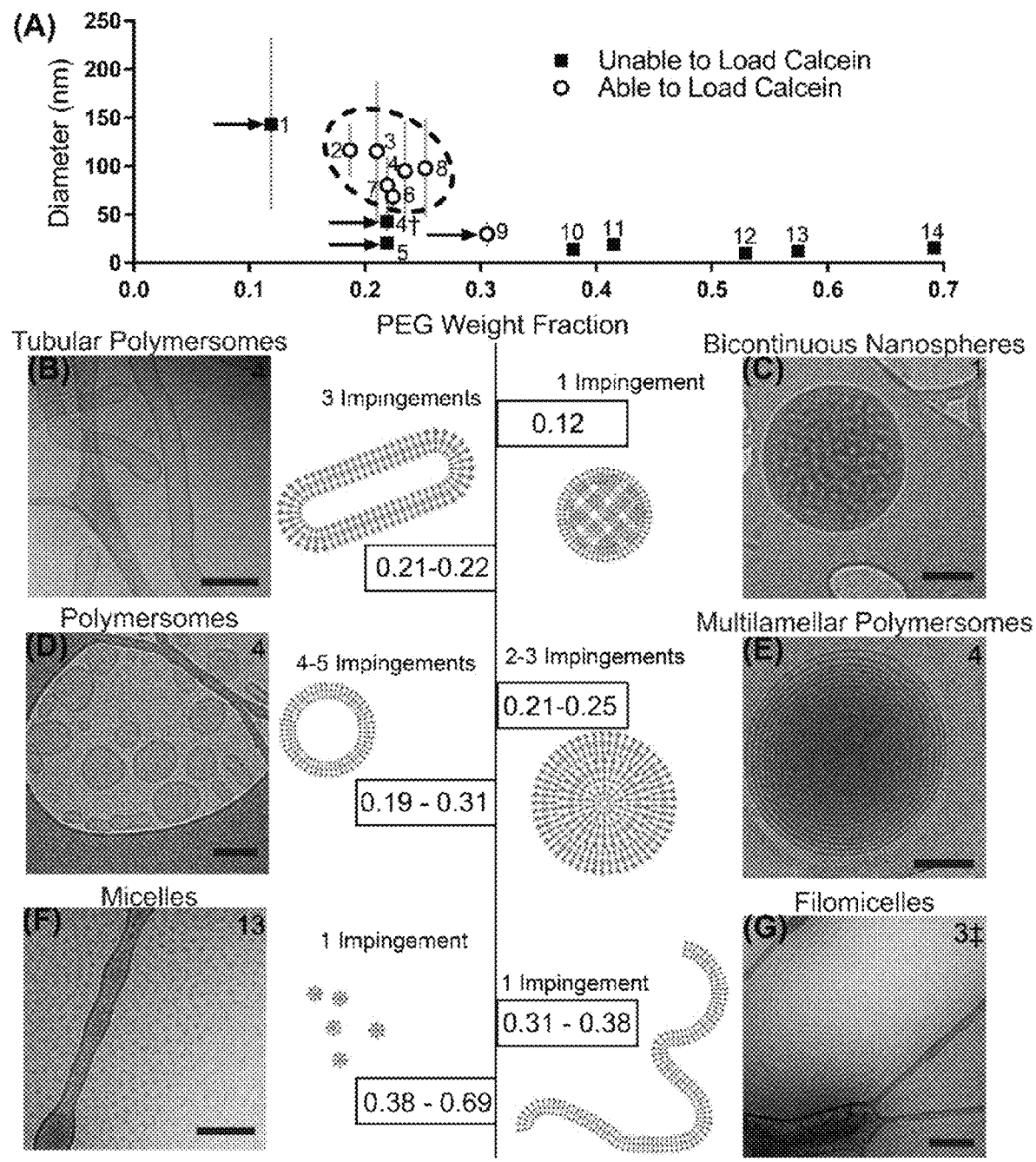
FIGS. 3A-3G show the relationship between PEG weight fraction and morphology.

Amphiphilic copolymers are comprised of sub-units or monomers that have different hydrophilic and hydrophobic characteristics. Typically, these sub-units are present in groups of at least two, comprising a block of a given character, such as a hydrophobic or hydrophilic block. Depending on the method of synthesis, these blocks could be of all the same monomer or contain different monomer units dispersed throughout the block, but still yielding blocks of the copolymer with substantially hydrophilic and hydrophobic portions. These blocks can be arranged into a series of two blocks (diblock) or three blocks (triblock), or more, forming the backbone of a block copolymer. In addition, the polymer chain may have chemical moieties covalently attached or grafted to the backbone. Such polymers are graft polymers. Block units making up the copolymer can occur in regular intervals or they can occur randomly making a random copolymer. In addition, grafted side chains can occur at regular intervals along the polymer backbone or randomly making a randomly grafted copolymer. The ratio of the hydrophobic to hydrophilic blocks of the copolymer will be selected such that the soluble and insoluble components are balanced and suitable aggregation for the desired architectures. Exemplary embodiments of various ratios are shown in FIG. 3A.

Suitable amphiphilic copolymers of the present invention are those polymers with a low glass transition temperature (Tg) hydrophobic block, typically below 0° C. or between about −70° C. and about 0° C. (i.e., less than about 10° C., 0° C., −5° C., −10° C., −20° C., −25° C., −30° C., −40° C., −45° C., −50° C., −60° C. or −70° C. and greater than about −70° C., −60° C., −50° C., −45° C., −40° C., −30° C., −25° C., −20° C., −10° C., or −5° C.). Polymers within this range will exhibit high mobility between polymer chains. Polymers which fit these characteristics include, without limitation, poly(ethylene glycol) (PEG), poly(propylene sulfide) (PPS), poly(ethylene sulfide), polycaprolactone, poly(dimethylsiloxane) and polyethylene. Polymers may also include chemical modifications or end caps. Chemical modification and end caps may include, but are not limited to, thiol, benzyl, pyridyl disulfide, phthalimide, vinyl sulfone, aldehyde, acrylate, maleimide, and n-hydroxysuccinimide groups. The chemical modification of the polymer may add a charged residue to the polymer or may be used to otherwise functionalize the polymer. In some embodiments of the present invention, the polymer is poly(ethylene glycol)-bl-poly(propylene sulfide) (PEG-bl-PPS). In one embodiment, the polymer is $PEG_{17}$-bl-$PPS_{30}$-Thiol.

In some embodiments of the organic phase solution, the Hildebrand solubility parameter ($\delta$) of the hydrophobic portion of the amphiphilic copolymer is matched to the solubility parameter of the water miscible organic solvent to increase the mobility of the polymer in solution. The proper organic process solvent will be selected based on the identity and characteristics of the amphiphilic copolymer selected. In one embodiment, the amphiphilic copolymer is PEG-bl-PPS (PPS $\delta$=18.6 $MPa^{1/2}$) and the organic solvent is THF ($\delta$=18.6 $MPa^{1/2}$). In some embodiments of the organic phase solution, the solubility parameter is dissimilar between the copolymer and the organic solvent which lowers chain flexibility and produces slower kinetics for nanostructure transitions. In one embodiment, the amphiphilic copolymer is PEG-bl-PPS (PPS $\delta$=18.6 $MPa^{1/2}$) and the organic solvent is DMF ($\delta$=24.8 $MPa^{1/2}$).

As used herein, the term "aqueous phase solution" refers collectively to the solution comprising an aqueous nonsolvent and optionally one or more target molecules. The aqueous solution can comprise an aqueous nonsolvent solution comprising pure water, a buffering agent, salt, colloid dispersant or inert molecule, or combinations thereof. The aqueous phase solution may comprise one or more buffers, one or more salts, and one or more supplemental additive agents, such as inert diluents, solubilizing agents, emulsifiers, suspending agents, adjuvants, wetting agents, reducing agents, isotonic agents, colloidal dispersants and surfactants. In some embodiments, the aqueous nonsolvent is phosphate-buffered saline (PBS). In some embodiments, the salt is a kosmotropic salt. In some embodiments, the buffer is selected form common buffers used for biochemical reactions and cell culture, including phosphate buffer saline (PBS), (4-(2-hydroxyethyl)-1-piperazineethanesulfonic acid) (HEPES), tris(hydroxymethyl)aminomethane (Tris), citric acid, and 3-(N-morpholino)propanesulfonic acid (MOPS). In some embodiments, the salt is a kosmotropic salt. In some embodiments, the salt is selected from the group consisting of, sodium chloride, ammonium acetate, potassium chloride, monopotassium phosphate, disodium phosphate, sodium acetate, and zinc chloride.

The aqueous phase solution is formulated in a manner sufficient to maintain the stability of any target agent suspended or dissolved therein. For example, it is envisioned that if the additive target agent is selected from the group consisting of a DNA molecule, an RNA molecule, and a protein molecule, the aqueous solution will have a proper pH and salinity such that the target molecule will maintain proper folding and stability while in solution. In some embodiments, the aqueous phase solution will have a physiologically relevant pH and salinity appropriate for loading biological macromolecules into the nanocarriers. In one embodiment, the aqueous phase solution comprises between about 0 mM and 200 mM salt. In one embodiment the aqueous phase solution comprises less than or equal to 150 mM salt. In one embodiment, the aqueous phase solution has a pH between about 2.0 and 12.0. In one embodiment the aqueous phase solution has a pH between about 5.0 and 9.0. In one embodiment the aqueous phase solution has a pH between about 7.0 and 8.0.

As used herein, the term "aqueous nonsolvent" refers to the water or other aqueous solvent solution present in the aqueous phase solution or in the reservoir solution. The amphiphilic copolymer is not solvent in the nonsolvent, and the nonsolvent acts to strip the water miscible organic solvent away from the amphiphilic copolymer during the process of flash nanoprecipitation.

In another aspect of the invention, nanocarriers are made and include one or more target molecules. The one or more target molecules may be added to the organic phase solution, the aqueous phase solution, the reservoir, or combinations thereof. In some embodiment, a target molecule is included with the amphiphilic copolymer in the organic phase solution. In some embodiments, the target molecule is present in the aqueous phase solution. In some embodiments, a first target molecule is included in the organic phase solution and a second target molecule is included in the aqueous phase solution. In some embodiments, the target molecule is included in the reservoir. The target molecule is combined with the amphiphilic copolymer in a ratio of 1:4 to 10:1 by weight or charge. In one embodiment, the target molecule is mixed with the amphiphilic copolymer in at least a 1:2 ratio by weight. Preferably the target molecules is present in the mixture after mixing at a concentration of at least 0.1% by weight, but more preferably the concentration of target molecule is at least 0.2% by weight. In some embodiments the target molecule is included at between 0.1% and 20% by weight, between 1% and 15% by weight or between 1.5% and 12% by weight. The temperature and the pressure of the organic phase solution, the aqueous phase solution or the mixture thereof can be altered to allow complete dissolution of both the amphiphilic copolymer and the target molecule while maintaining a liquid phase.

As used herein, the term "target molecules" refers to any molecule to be loaded into the nanocarriers according to embodiments of the present invention. The target molecule may be hydrophobic, hydrophilic, lipophilic or amphiphilic. The target molecule may include hydrophilic macromolecules such as RNA, DNA, plasmids, peptides, antibodies, proteins, fluorophores, carbohydrates, small molecule drugs, water soluble synthetic polymers and combinations thereof. Target molecules also include adhesive or targeting moieties such as cell specific antibodies which target the nanocarrier to a specific cell type or target of interest. Examples of other target molecules that may be added to nanoparticles by this process can be selected from, but are not limited to, the known classes of drugs including immunosuppressive agents such as cyclosporins (cyclosporin A), immunoactive agents, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, anti-oxidants, preservatives, vitamins, nutrients, adjuvants, antigents, MRI contrast agents, metal (i.e., gold, iron oxide, and the like), nanomaterials (i.e., quantum dots, micelles), temperature sensitive polymers (i.e., Poly(N-isopropylacrylamide)), polymer-drug conjugates, and biologics (referring collectively to any carbohydrate, protein, polypeptide, nucleic acid, combinations thereof and the like). Target molecules may also include combinations of, complexes of, mixtures of or other associations of any of the target molecules listed.

In some embodiments, the methods described herein support simultaneous loading of both hydrophobic and hydrophilic target molecules. Without being bound by any particular theory, it is envisioned that hydrophobic target molecules may be loaded into the polymersome or nanocarrier membrane while hydrophilic target molecules may be loaded into aqueous lumen formed with in the polymersome or nanocarrier. It is also envisioned that the loaded molecules, in particular loaded hydrophilic biological macromolecules, such as DNA, RNA, and proteins, remain active following lysis from the nanocarrier or polymersome formed by the methods described herein.

The loading efficiency of the target molecule in the nanocarriers by the methods of the present invention is measured as the ratio of target molecule encapsulated within the nanocarrier to the total amount of target molecule available for loading in the initial solution. The loading efficiency is typically greater than about 40% for both proteins and hydrophobic molecules (i.e., about 35%, about 40%, about 45%, about 50%, about 60%, about 70%, about 80%, about 85%, about 90%, or any percentages in between). In some embodiments of the invention, the loading efficiency is greater than at least 45%.

One or more supplemental additives can be added to the organic phase solution or aqueous phase solution or to a stream of nanoparticles after formation by flash precipitation to tailor the resultant properties of the nanoparticles or for use in a particular indication. Examples of supplemental additives include inert diluents, solubilizing agents, emulsifiers, suspending agents, adjuvants, wetting agents, reducing agents, sweetening, flavoring, and perfuming agents, isotonic agents, colloidal dispersants and surfactants such as, but not limited to, a charged phospholipid such as dimyristoyl phophatidyl glycerol; alginic acid, alignates, acacia, gum acacia, 1,3 butyleneglycol, benzalkonium chloride, collodial silicon dioxide, cetostearyl alcohol, cetomacrogol emulsifying wax, casein, calcium stearate, cetyl pyridiniumn chloride, cetyl alcohol, cholesterol, calcium carbonate, Crodestas F-110®, which is a mixture of sucrose stearate and sucrose distearate (of Croda Inc.), clays, kaolin and bentonite, derivatives of cellulose and their salts such as, but not limited to, hydroxypropyl methylcellulose (HMPC), carboxymethylcellulose sodium, carboxymethylcellulose and its salts, hydroxypropyl celluloses, methylcellulose, hydroxyethylcellulose, hydroxypropylcellulose, hydroxypropylmethylcellulose phthalate, noncrystalline cellulose; dicalcium phosphate, dodecyl trimethyl aminonium bromide, dextran, dialkylesters of sodium sulfosuccinic (e.g. Aerosol OT® of American Cyanamid), gelatin, glycerol, glycerol monostearate, glucose, p-isononylphenoxypolt-(glycidol), also known as Olin 10-G® or surfactant 10-G® (of Olin Chemicals, Stamford, Conn.); glucamides such as octanoyl-N-methylglucamide, decanoyl-N-methylglucamide; heptanoyl-N-methylglucamide, lactose, lecithin (phosphatides), maltosides such as n-dodecyl β-D-maltoside; mannitol, magnesium stearate, magnesium aluminum silicate, oils such as cotton seed oil, corn germ oil, olive oil, castor oil, and sesame oil; paraffin, potato starch, polyethylene glycols (e.g., the Carbowaxs 3350® and 1450®, and Carbopol 9340® of Union Carbide), polyoxyethylene alkyl ethers (e.g. macrogol ethers such as cetomacrogol 1000), polyoxyethylene sorbitan fatty acid esters (e.g. the commercially available Tweens® of ICI specialty chemicals), polyoxyethylene castor oil derivatives, polyoxyethylene sterates, polyvinylalcohol (PVA), polyvinylpyrrolidone (PVP), phosphates, 4(1,1,3,3-tetramethylbutyl) phenol polymer with ethylene oxide and formaldehyde, (also known astyloxapol, superione, and triton), all poloxamers and polaxamines (e.g., Pluronics F68LF®, F87®, F108® and tetronic 908® available from BASF Corporation Mount Olive, N.J.), pyranosides such as n-hexyl β-D-glucopyranoside, n-heptyl β-D-glucopyranoside; n-octyl-β-D-glucopyranoside, n-decyl β-D-glucopyranoside; n-decyl β-D-maltopyranoside; n-dodecyl β-D-glucopyranoside; quaternary ammonium compounds, silicic acid, sodium citrate, starches, sorbitan esters, sodium carbonate, solid polyethylene glycols, sodium dodecyl sulfate, sodium lauryl sulfate (e.g., Duponol P® of DuPont corporation), steric acid, sucrose, tapioca starch, talc, thioglucosides such as n-heptyl β-D-thioglucoside, tragacanth, triethanolamine, Triton X-200® which is a alkyl aryl polyether sulfonate (of Rhom and Haas); and the like. The inert diluents, solubilizing agents, emulsifiers, adjuvants, wetting agents, isotonic agents, colloidal dispersants and surfactants are commercially available or can be prepared by techniques know in the art. In some embodiments, the excipients are selected from the group consisting of amphiphilic polymers, urea, chaotropic salts, and kosmotropic salts. The properties of many of these and other pharmaceutical excipients suitable for addition to the organic phase solution and aqueous phase solution before or after mixing are provided in Handbook of Pharmaceutical Excipients, 7rd edition, editor Arthur H. Kibbe, 2000, American Pharmaceutical Association, London, the disclosure of which is hereby incorporated by reference in its entirety.

Colloidal dispersants or surfactants can be added to colloidal mixtures such as a solution containing nanoparticles to prevent aggregation of the particles. In one embodiment of the invention, a colloidal dispersant is added to either the organic phase solution or aqueous phase solution prior to mixing. In one embodiment, the colloidal dispersant can include a gelatin, phospholipid or pluronic. The dispersant is typically added in a ratio up to 2:1 with the one or more target molecule by weight. The use of a colloidal dispersant can prevent nanoparticles from growing to a size that makes them unusable for the use in the treatment of subjects.

In another embodiment of the invention, the target molecule is mixed with the amphiphilic copolymer with a supplemental seeding molecule. The inclusion of a supplemental seed molecule in the process solvent facilitates the creation of nanoparticles upon micromixing with the nonsolvent. Examples of a supplemental seed molecule include, but are not limited to, a substantially insoluble solid particle, a salt, a functional surface modifier, a protein, a sugar, a fatty acid, an organic or inorganic pharmaceutical excipient, a pharmaceutically acceptable carrier, or a low molecular weight oligomer.

In one embodiment, a supplemental surfactant can be added to the organic phase solution or the aqueous phase solution. This process can be performed with amphiphilic copolymer alone or with an organic phase solution or aqueous phase solution containing one or more target molecule.

Preferably the nanocarrier compositions containing one or more amphiphilic copolymers, with or without one or more target molecules, and with or without one or more supplemental additives which are produced by a flash precipitation by the methods of the present invention have an average size less than 1060 nm and more preferably less than about 700 nm, alternatively less than about 500, alternatively less than about 400, alternatively less than about 200, alternatively less than about 100, alternatively less than about 40 nm. In some embodiments the size is between 80-150 nm. For filamentous nanocarrier architectures, the average diameter is between 5 to 100 nm (i.e., between 10-90 nm, between 15-80 nm, and between 20-70 nm) with lengths of a micron or greater. The average size is on a weight basis and is measured by light scattering, microscopy, or other appropriate methods.

The nanocarriers produced by the flash precipitation process of embodiments of the present invention can be post processed to yield a sterile aqueous or non-aqueous solution or dispersion or could be isolated, such as via lylophilization and autoclaving, to yield a sterile powder for reconstitution into sterile injectable solutions or dispersions. The nanoparticles can be combined with other acceptable compounds for parenteral injection such as but not limited to one or more of the following: water, ethanol, propyleneglycol, polyethyleneglycol, glycerol, vegetable oils, and ethyl oleate. Supplemental additives suitable for parenteral injection can also be used to tailor the composition to that suitable for a specific purpose.

In one embodiment, the stream of nanocarriers produced via flash precipitation, is distilled to remove any toxic solvents and sterile filtered using a 0.22 µm nominal pore size filter to yield a sterile solution. In another embodiment, the organic phase solution and aqueous phase solution are sterilized prior to use and are flash precipitated in a sterile environment to produce a sterile formulation. In some embodiments, any post processing is also performed under sterile conditions.

The nanocarrier compositions produced by the methods described herein via flash precipitation may also contain supplemental additives useful for preserving, wetting, emulsifying, or dispensing the pharmaceutical composition. Prevention of the growth of microorganisms can be ensured by various antibacterial and antifungal agents, such as, but not limited to, sorbic acid, parabens, phenol, chlorobutanol. It may be desirable to add an antioxidant such as tocopherol or the like, or it may be desirable to include isotonic agents, such as, but not limited to, sugars or sodium chloride.

In one embodiment, the nanocarriers formed via flash precipitation are isolated via distillation to remove toxic solvents such as THF, a supplemental additive is added, such as the cryoprotectant sucrose or trehelose, and the material is lyophilized to obtain a powder.

In one embodiment, the nanocarrier compositions produced by the flash precipitation methods of the present invention are formulated into a solid dosage form for oral administration such as capsules, tablets, pills, powders, and granules, or the like. In such solid dosage forms, the nanocarrier composition is admixed with one or more supplemental additives falling into the following classes such as, but not limited to, lubricants, buffering agents, wetting agents, adsorption, inert excipients, binders, disintegrating agents, solution retarders, accelerators, adsorbents, or fillers or extenders or other components commonly used by those skilled in the art for production of solid dosage forms.

In an embodiment, a composition comprising nanocarriers of the present invention is a potent pharmaceutical containing one or more amphiphilic copolymers, with or without one or more target molecules, and with or without one or more supplemental additives which are produced by a flash precipitation method of the present invention. In some embodiments, the composition is a solid dosage form and due to its nanoparticulate size it is evenly dispersed throughout said solid dosage form admixture and yields a high content uniformity (quantity of material in each dose) not obtained if the drug was microparticulate.

In one embodiment, the nanocarrier compositions produced by the flash precipitation methods of the present invention are formulated into a pharmaceutically acceptable liquid dosage form for oral administration such as a syrup, solution, emulsion, suspension, or elixir. In addition to the amphiphilic copolymer nanocarriers, the liquid dosage forms may comprise inert diluents, solubilizing agents, oils, emulsifiers, adjuvants suspending agents, sweeteners, wetting agents, flavoring agents, perfuming agents or other compounds commonly used by those skilled in the art.

The nanocarrier compositions containing one or more amphiphilic copolymers, with or without one or more target molecules, and with or without one or more supplemental additives which are produced by the flash precipitation methods of the present invention can be administered to a subject, for example, humans and animals, via a number of means including, but not limited to, orally, rectally, parenterally (intravenous, intramuscular, or subcutaneous), intracisternally, intravaginally, intraperitoneally, locally (in the form of powders, ointments or drops) or as a buccal or nasal spray.

The nanocarriers produced by the methods of the present invention can also be used in immunotheranostic or theranostic application which combine immunotherapy and diagnostics. It is envisioned that target molecules used for immunotherapy can be incorporated along with target molecules used for imagine and diagnostics into a single nanocarrier or a composition comprising nanocarriers for theranostic treatments.

An advantage of the methods of embodiments of the present invention is the ability to encapsulate hydrophilic target molecules without the requirement of further processing. For example, the methods described herein require no extrusion steps. As such, the methods of the present invention can be carried out over a short period of time (e.g. over minutes via FNP as opposed to days via thin film hydration followed by extrusion). In some embodiments, the nanocarriers are assembled in 5 minutes or less.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates flash nanoprecipitation and loading of nanocarrier structures of PEG-bl-PPS with a variety of target molecules including rapamycin, fluorescent dyes, dextran among others. Protocols for FNP employ multi-stream mixers in which an organic solution of solubilized hydrophobic drug and an amphiphilic block copolymer dissolved in a water-miscible common solvent are impinged upon an aqueous solution briefly under turbulent conditions and subsequently introduced into an aqueous reservoir (FIG. 1A). The supersaturated conditions generated by the turbulent mixing induces precipitation and nucleation of the hydrophobic solute and coprecipitation of the block copolymer for stabilization of monodisperse nanoparticles with hydrophobic drug cores. Mixing occurs over millisecond timescales and is followed by transfer to a reservoir of aqueous nonsolvent to strip away solvent still associating with the aggregated drug and block copolymer. While micelles can form within nanoseconds, the combined entropically and enthalpically driven transition in aggregate morphology to filomicelles, bilayer sheets and vesicles occurs over much longer timescales. The glass transition (Tg) of the amphiphile's hydrophobic block influences chain flexibility and as a result the timescale of aggregate shape transformations, which can range from hours for glassy high Tg polymers to milliseconds for low Tg polymers. Thus the rapid mixing followed by an immediate increase in water content within the reservoir during FNP effectively minimizes the chain mobility of the hydrophobic copolymer blocks to stably lock the molecular orientation of the assembly, and this is particularly effective for high Tg polymers like polystyrene. It was determined that the organic solvent must be removed from the assembly quickly to prevent nanoparticle instability and ripening, which can be achieved via flash solvent evaporation or using aqueous reservoirs with large volumes to decrease the solvent concentration. While recent focus has been placed on this process of competitive aggregation for the scalable loading of nanoparticles with hydrophobic drugs, FNP was originally applied to achieve rapid changes in solvent quality for homogenous precipitation and self-assembly of block copolymers to investigate the mechanism and kinetics of micellization. However, FNP has not been shown to produce more complex self-assembled soft nanoarchitectures such as polymer vesicles (i.e. polymersomes) that would be capable of loading hydrophilic therapeutics until the present Example.

Structurally analogous to liposomes, polymersomes possess enhanced physical and chemical stability and have emerged as versatile drug delivery vehicles. Polymersomes are comprised of three separate topological regions: an inner aqueous cavity, a hydrophobic membrane and an external surface that together allow simultaneous transport of both water soluble and lipophilic payloads as well as incorporation of adhesive and targeting moieties. A key advantage of the inner lumen is the ability to encapsulate and protect sensitive biologics, such as enzymes and nucleic acids. The size and shape of these nanocarriers impacts their biodistribution, systemic clearance, cellular internalization, optical properties and overall therapeutic potential. Aggregate morphology can be specified by synthesizing block copolymers with a particular hydrophilic weight fraction (typically >45% for polymersomes), kinetically trapping metastable intermediate structures during self-assembly or modulating the vesicles after formation often using shear forces or osmotic pressure gradients. These methods have resulted in a wide range of nanostructures with unique properties and applications, including tubule polymersomes, multilamellar nested vesicles and bicontinuous nanostructures. High throughput synthesis of these structures remains a challenge, as most of these morphologies can require days for formation and represent only a small fraction of the assembled aggregate population. The most commonly used methods of polymersome formation from di- or tri-block polymers are diverse variations of thin film hydration, solvent dispersion and microfluidics. Of these methods, thin film hydration and microfluidics have proven to be most amenable to the loading of protein biologics, as they avoid extensive exposure of payloads to organic solvents that can disrupt protein conformation and activity. Unfortunately, thin film hydration cannot control for vesicle size and requires additional processing steps, primarily by extrusion through nanoporous membranes. The current methods do not require an extrusion step providing a distinct advantage over prior methods. Microfluidics is low throughput (μL/min) and fabricates primarily microscale vesicles due to restrictions on channel dimensions. Thus although numerous methods have been developed for polymersome formation, a need still exists for facile, rapid, high throughput methods capable of both specifying nanostructure morphology and loading diverse bioactive payloads.

Poly(ethylene glycol)-bl-poly(propylene sulfide) (PEG-bl-PPS) is a highly versatile self-assembling block copolymer that can be engineered to stably form polymersomes and a variety of other nanoarchitectures. This ability is in part due to the low Tg of PPS (227 K), which permits high chain flexibility at room temperature and rapid transitions between metastable aggregate morphologies. Depending on the molecular weight ratio of the hydrophilic PEG and hydrophobic PPS blocks as well as the method of assembly, PEG-bl-PPS can assemble into micelles, vesicles and filomicelles. Even at relatively low MW, PEG-bl-PPS aggregates are highly stable in dilute aqueous solutions as evidenced by an octanol/water partition coefficient (log P) of 13.07 and a critical micelle concentration of $3 \times 10^{-6}$ M. This stability has allowed PEG-bl-PPS nanocarriers to support the delivery of a variety of therapeutic molecules and fluorophores both in vitro and in vivo. Furthermore, the oxidation-sensitivity of PPS provides a means for controlled degradation and payload release via photo-oxidation or cell-derived ROS as well as systemic clearance of the block copolymer through the kidneys. Small scale assembly and loading of PEG-bl-PPS nanocarriers have been achieved via thin film hydration, direct hydration, solvent extraction, and freeze thaw-cycling, which, in the case of polymersomes, subsequently requires extensive extrusion to form monodisperse nanocarriers.

The inventors discovered that under the standard conditions of use, FNP may serve as a scalable and rapid method to assemble and load soft nanoarchitectures in addition to micelles when coupled with a block copolymer containing a hydrophobe with a sufficiently low Tg, such as PEG-bl-PPS. The rapid millisecond timescale of PEG-bl-PPS transitions between metastable intermediate morphologies more closely matches the mixing time of FNP, which may allow kinetic entrapment of nanostructures that are otherwise impossible to observe outside of molecular dynamics models. Here, the inventors demonstrate that by adjusting the aqueous solution conditions, number of impingements and reservoir volume, FNP can rapidly assemble PEG-bl-PPS block copolymers into bicontinuous nanospheres, filomicelles and vesicular, multilamellar and tubular polymersomes. Many of these nanocarrier morphologies are difficult to achieve reproducibly and have not been previously reported for PEG-bl-PPS copolymer systems. The inventors additionally demonstrate that multiple impingements of polymersomes allowed further modulation of the obtained nanostructure and a rapid method of decreasing polydispersity, which presents an alternative to more time-intensive extrusion. Furthermore, this Example demonstrates that diverse hydrophilic molecules, including proteins, could be stably encapsulated within polymersomes via FNP and retain their bioactivity following release. Co-loading of therapeutics with fluorescent dyes allowed rapid formation of theranostic polymersomes. As an immunotheranostic (i.e., combining immunotherapy and diagnostics) application of this methodology, we demonstrate enhanced immunosuppression of T cells by low dosage subcutaneous (SC) injection of rapamycin loaded within fluorescent polymersomes. Flow cytometric analysis allowed association of the therapeutic effect with intracellular delivery to lymph node resident and splenic macrophages. Our results enhance the versatility of FNP and may provide a facile high throughput method to fabricate drug-loaded polymersomes for biomedical applications.

Results and Discussion

Formation of Polymersomes Via Flash Nanoprecipitation

The rate of self-assembly strongly influences the nanoarchitecture of block copolymer aggregates, and for FNP, at a standard temperature (i.e., a temperature between 0° C. and 37° C. for nanocarriers that may comprise biologics), is primarily determined by the polymer concentration, steric stabilization of the hydrophilic block, similarity in solubility parameters of the common solvent and non-solvent for both the hydrophilic and hydrophobic blocks, and the rate of removal of the solvent upon addition to the non-solvent reservoir. Although many of these conditions have been optimized for specific block copolymer chemistries and drug loading, several standard practices have been universally adopted for FNP protocols to achieve stable kinetically trapped nanoparticles. These include the use of tetrahydrofuran (THF) and pure water as the solvent and nonsolvent, respectively, as well as large reservoir-to-solvent volume ratios. Decreasing the polymer concentration as well as solvent selection have been employed to both specify nanoparticle size and to enhance payload complexation with the block copolymer. The inventors therefore hypothesized that the use of a diblock copolymer with an appropriate hydrophilic to hydrophobic block molecular weight ratio and sufficiently low Tg may be induced to form polymersomes under the millisecond mixing conditions of FNP. The Tg and Hildebrand solubility parameter ($\delta$) for PPS ($\delta$=17.9 MPa$^{1/2}$) both suggested PEG-bl-PPS to be well suited for the kinetic entrapment of metastable aggregate morphologies using standard protocols for FNP in a confined impingement jets (CIJ) mixer, which involves the impingement of THF ($\delta$=18.6 MPa$^{1/2}$) with an aqueous solution at a flow rate of $1.2 \times 10^{-6}$ m$^3$/s (FIG. 1A).

Figures 6A, 6B, 6C, 6D:
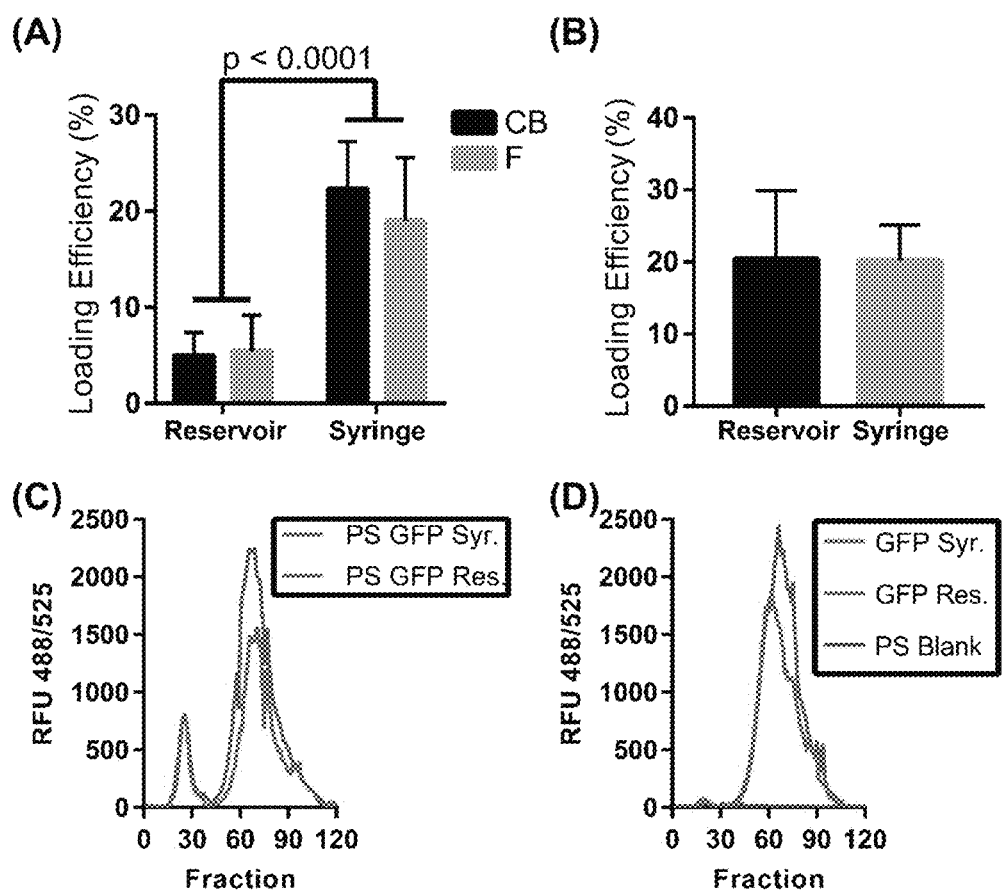
FIGS. 6A-6D show efficiency of loading via syringe or reservoir. (A) Loading efficiency of fluorescently-labeled 10 kDa dextrans (CB=cascade blue, F=fluorescein). Error bars represent standard deviation, n=6. (B) Loading efficiency of GFP when loaded via either syringe or reservoir. Error bars represent standard deviation, n=3. (C) Fluorescence of sepharose CL-6B column separated GFP-loaded polymersomes loaded via syringe or reservoir, 200 μL fractions. (D) Fluorescence of sepharose CL-6B column separated GFP processed via FNP through the syringe or reservoir without PEG-bl-PPS copolymer, as a control. Included is a trace of blank polymersomes, for reference.

In order to investigate the potential for FNP to form polymersomes, the inventors used PEG$_{17}$-bl-PPS$_{30}$-Thiol, a polymer already demonstrated to form polymersomes via both thin film rehydration and solvent dispersion. This copolymer was dissolved in THF, impinged at $1.2 \times 10^{-6}$ m$^3$/s against 1xPBS within a CIJ mixer and introduced into a 1xPBS aqueous reservoir (FIGS. 1A and 1B). The resulting assemblies were analyzed via cryoTEM and nanoparticle tracking analysis (NTA) to respectively assess their morphology and size, and were found to consist of polymersomes (FIG. 1C). The use of a PBS salt solution served two purposes. First, vesicular nanoarchitectures maintain osmotic balance with downstream biological fluids in which they will be applied, or risk rupture. Second, the inventors suspected that decreasing the PEG solubility and resulting rate of steric stabilization with a kosmotropic salt solution would allow increased chain mobility for vesicle assembly. To further enhance chain mobility, FNP was performed under solvent conditions which normally result in unstable Ostwald ripening and coalescence. Specifically, the volume ratio of THF/aqueous dilution within the reservoir was only 1:6, while ratios of 1:20 are often suggested in other implementations of FNP for rapid solvent extraction to kinetically trap micellar nanostructures. Use of these conditions (decreased PEG solubility and increased organic solvent concentration in the reservoir) likely provided a system of dynamic self-assembly that allowed continued assembly of the PEG$_{17}$-bl-PPS$_{30}$-Thiol into polymersomes within the aqueous reservoir. This was later verified by the observed loading of fluorescently tagged 10 kDa dextran from the reservoir into the polymersome lumen (FIG. 6A). Switching the solvent to dimethylformamide ($\delta$=24.8 MPa$^{1/2}$) resulted in the formation of micelles for copolymers that were initially found to assemble vesicles when THF was used as the common solvent. This result may be due the lower similarity in solubility parameters between DMF and PPS relative to THF and PPS, which would lower chain flexibility and produce slower kinetics for nanostructure transitions. Slowing the transition kinetics through the use of less similar common solvents is known to promote micelle instead of vesicle formation for other block copolymer systems.

Multiple Impingements Reduce Polymersome Diameter and Polydispersity

Figures 2A, 2B, 2C, 2D, 2E, 2F, 2G:
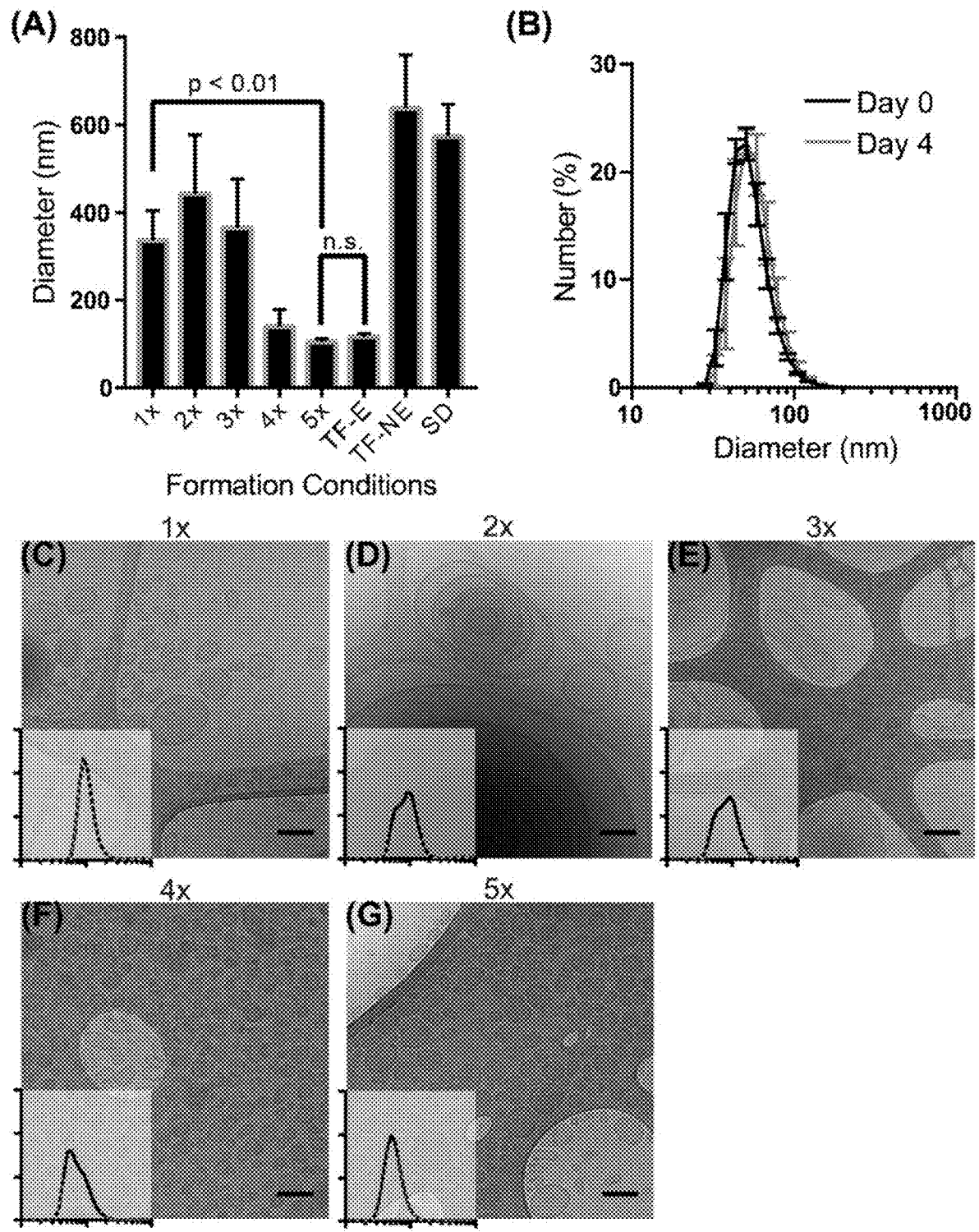
FIG. 2A-2G show fabrication of monodisperse polymersomes via flash nanoprecipitation.
Figure 7:
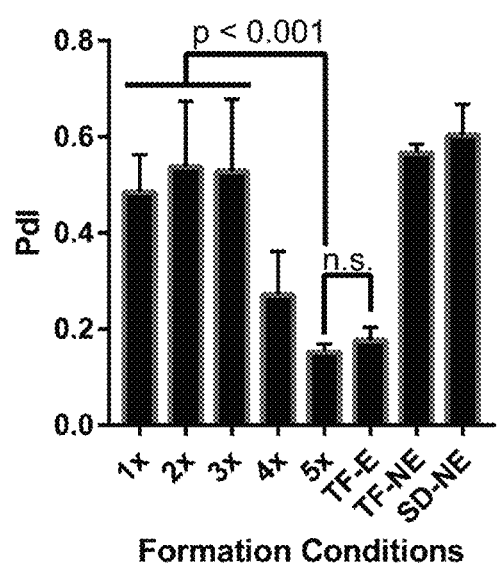
FIG. 7 shows DLS mean polydispersity (PdI) of polymersomes formed after multiple impingements (1×-5×), or formed by thin film (TF) or solvent dispersion (SD) with (E) or without (NE) extrusion. Error bars are standard error, n=5.

Nanocarriers used in biomedical applications are typically expected to have a low polydispersity for therapeutic reproducibility and consistency in biodistribution and cellular targeting. The polymersomes formed by FNP (Table 1) demonstrated a polydispersity index (PDI) that ranged from 0.220 to 0.634, which is similar to polymersomes formed by solvent dispersion and thin film rehydration that require subsequent extrusion through membranes with nanoscale porosity to achieve monodisperse vesicles (FIGS. 2A and 7). The extrusion process can be time-consuming, result in the loss of product, potentially reduce loading efficiency, and presents an opportunity for the introduction of contaminants and endotoxin. Shear flow has been demonstrated to be a viable and underexplored mechanism to influence the shape and polydispersity of metastable aggregate states. Since vesicle uniformity has been found to improve with increasing shear rate, we hypothesized that repeated impingement of polymersomes within the CIJ mixer under conditions promoting continued fluidity of the PPS membrane may decrease vesicle polydispersity without the need for subsequent extrusion.

TABLE 1

Relationship between PEG weight fraction ($f_{PEG}$) and morphology.

| # | PEG DoP | PPS DoP | $f_{PEG}$ | End Capping | Com/Aqu Solv | D (nm) | PDI | Morphology |
|---|---------|---------|-----------|-------------|--------------|--------|-----|------------|
| 1 | 17 | 75 | 0.119 | Thiol | THF/PBS | 143.13 | 0.62 | BN, M, P |
| 2 | 17 | 44 | 0.187 | Benzyl | THF/PBS | 116.53 | 0.24 | P |
| 3 | 17 | 38 | 0.21 | Thiol | THF/PBS | 115.29 | 0.63 | **P, MLP\*, TP\*** |
| 3‡ | | | | | THF/Water | N/A | N/A | FM |
| 4 | 17 | 36 | 0.219 | Thiol | THF/PBS | 80.51 | 0.37 | **P, MLP\*, TP\*** |
| 4† | | | | | DMF/PBS | 41.53 | 0.31 | **M, P\*\*** |
| 5 | 45 | 96 | 0.219 | Benzyl | THF/PBS | 20.54 | 0.25 | M |
| 6 | 17 | 35 | 0.224 | Pyridyl Sulfide | THF/PBS | 68.58 | 0.22 | **P, MLP\*, TP\*** |
| 7 | 17 | 33 | 0.235 | Thiol | THF/PBS | 95.06 | 0.55 | P, MLP\* |

TABLE 1-continued

Relationship between PEG weight fraction ($f_{PEG}$) and morphology.

| # | PEG DoP | PPS DoP | $f_{PEG}$ | End Capping | Com/Aqu Solv | D (nm) | PDI | Morphology |
|---|---|---|---|---|---|---|---|---|
| 8  | 17 | 30 | 0.252 | Thiol      | THF/PBS | 97.96 | 0.52 | P, MLP* |
| 9  | 17 | 23 | 0.305 | Thiol      | THF/PBS | 29.78 | 0.43 | M, P, FM |
| 10 | 45 | 44 | 0.38  | Benzyl     | THF/PBS | 14.28 | 0.33 | M, FM |
| 11 | 45 | 38 | 0.415 | Phthalimide| THF/PBS | 19.03 | 0.29 | M |
| 12 | 45 | 24 | 0.529 | Benzyl     | THF/PBS | 10.13 | 0.38 | M |
| 13 | 45 | 20 | 0.574 | Benzyl     | THF/PBS | 12.75 | 0.3  | M |
| 14 | 45 | 12 | 0.692 | Benzyl     | THF/PBS | 15.43 | 0.43 | M |

Com/Aq Solv = Common/Aqueous Solvents used during the impingement process.
M = Micelles, FM = Filomicelles, BN = Bicontinuous Nanospheres, P = Polymersomes, MLP = Multilamellar Polymersomes, TP = Tubular Polymersomes.
Predominant population(s) shown in bold.
*Population only found after multiple impingements.
**Very rare population.
DLS diameter and polydispersity data not available for samples predominantly composed of filomicelles, i.e. sample 3‡.

We found that multiple impingements through the CIJ mixer both decreased the mean polymersome diameter and lowered the PDI to levels achievable by extrusion (FIGS. 2A and 7). To maintain high levels of the common solvent within hydrophobic PPS membranes for continued chain flexibility, we impinged a PEG-bl-PPS solution in THF against 1×PBS, collected the resulting mixture without diluting in a reservoir, evenly divided the THF/polymersome/PBS solution between the CIJ mixer syringes and repeated the impingement. As no reservoir was used, the volume remained constant, and the impingement could be repeated multiple times over the course of a several minutes without sample loss. Unexpectedly, the diameter and PDI increased over the first two repeat impingements (2× and 3×), before reducing significantly in the following two impingements (4× and 5×) (FIGS. 2A and 7). By the fifth impingement, there was no statistical difference in the diameter or PDI between FNP polymersomes and polymersomes formed by thin film hydration that were subsequently extruded through a 0.1 μm filter. Furthermore, 5× impinged polymersomes remained stable for days and demonstrated no detectable change in PDI (FIG. 2B). This change in the distribution of sizes can be observed by cryoTEM from the first impingement to the fifth and final impingement (FIGS. 2C-2G). While the first impingement generated primarily unilamellar and some rare multilamellar polymersomes ranging between 50 nm to nearly a micron in diameter, the 5× impinged polymersomes were monodisperse (PDI<0.15) and all possessed a single bilayer (FIG. 2G). Interestingly, the 2× and 3× polymersome populations were composed of large, multilamellar, and/or tubular polymersomes (FIGS. 2D, 2E, 10C and 10E). Tubular polymersomes have been predicted in simulations of polymersome formation under conditions of shear flow. Multilamellar vesicles may be a result of multiple fusion events induced by increased polymersome collisions under conditions of turbulent flow while PPS chains remain fluid and swollen with THF. Since no changes in vesicle polydispersity or structure were observed after 5 impingements, it is possible that continued diffusion of THF out of the PPS domains reduced chain flexibility sufficiently to prevent polymersome fusion. In silico simulations of these events will be required to verify our hypotheses. We found this protocol of repeated impingements to support the gram-scale production of monodisperse polymersomes within a matter of minutes, which is a task that could require days to weeks to achieve by alternative fabrication methods such as thin film hydration and extrusion.

PEG-Bl-PPS Copolymers can Form Numerous Nanoarchitectures Via Flash Nanoprecipitation PEG-bl-PPS can self-assemble into several nanoarchitectures simply by tuning the PEG weight fraction ($f_{PEG}$). Using thin film hydration, $f_{PEG}$ between 0.20 and 0.30 form polymersomes, $f_{PEG} \sim 0.38$ forms filomicelles and $f_{PEG} > 0.40$ generally results in spherical micelles (FIG. 1B). In order to determine whether there is a similar connection between fPEG and morphology when polymersomes are formed by FNP, we synthesized the polymers listed in Table 1 and assessed their assembly into nanostructures using cryogenic electron microscopy (FIG. 3). These polymers were impinged against a 40 mM calcein solution in 1×PBS, as calcein is a water-soluble dye and its encapsulation would confirm the formation of vesicle structures, as opposed to the lipophilic cores of micelles and filomicelles. The diameters and calcein-loading ability of the assembled nanocarriers are shown in FIG. 3A. Flash nanoprecipitated polymersomes were found to occupy a space characterized by diameters ranging from 50-200 nm and PEG weight fractions from 0.187-0.305, similar to that for thin film rehydration (FIG. 3A, dotted oval). Copolymers 10-14 ($f_{PEG} > 0.40$) were found to form primarily micelles, with a small population of filomicelles detected in the copolymer 10 sample. While copolymer 3 assembled polymersomes using PBS as the aqueous nonsolvent, switching to pure water resulted in the generation of filomicelles, likely due to the increased steric stabilization of the PEG corona (FIG. 3G and Table 1).

Figures 8A, 8B:
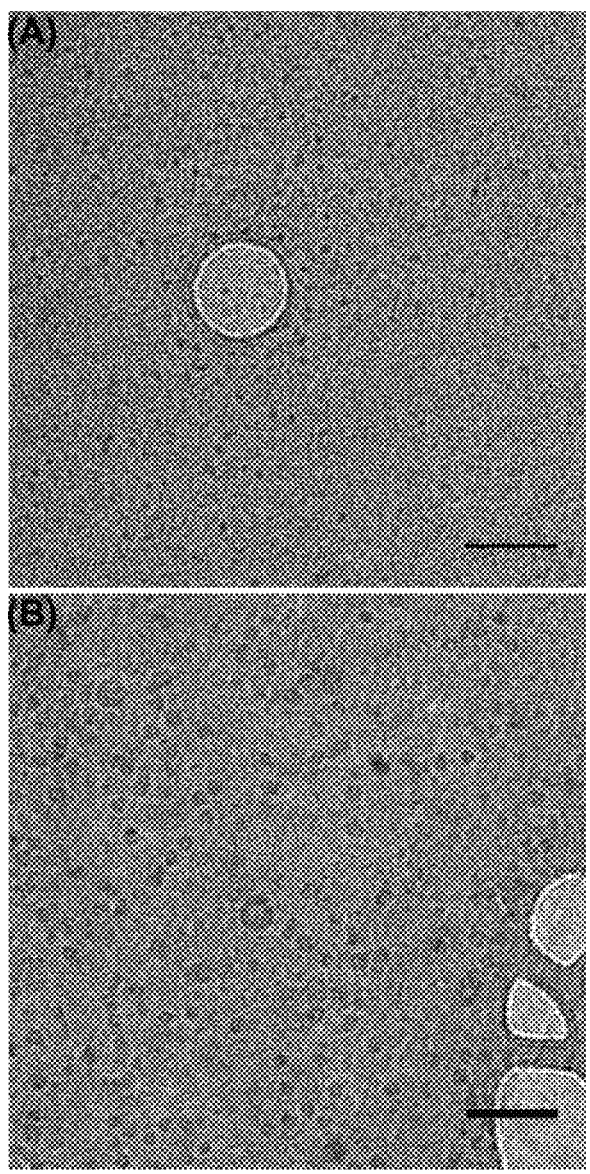
FIGS. 8A-8B show CryoTEM images of copolymers 5 and 9. (A) Micelles were formed by copolymer 5. (B) Micelles and occasional polymersomes were formed by copolymer 9. All scale bars represent 100 nm.
Figure 9:
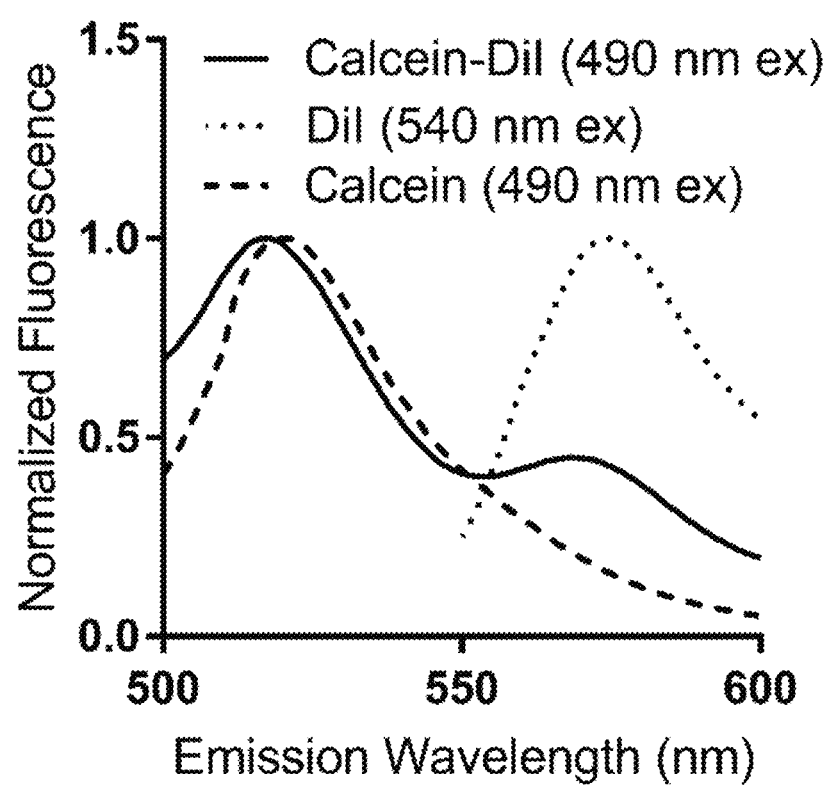
FIG. 9 shows emission spectra of calcein-DiI dual loaded polymersomes. Calcein-DiI polymersome emission (490 nm excitation) is represented by the solid black line. Calcein and DiI emission spectra are included in the plot for reference.

The three copolymers 1, 4, 5 and 9 (FIG. 3A, arrows), did not follow the previously described trends. Copolymer 1 failed to load calcein and was outside of the polymersome-forming range, yet had a diameter similar to that of polymersomes. CryoTEM imaging revealed these nanostructures to be monodisperse bicontinuous nanospheres (FIG. 3C and FIG. 10D), which is a nanostructure rarely formed from diblock copolymers in a controlled fashion FNP may therefore present a rapid and scalable alternative method of formation of polymeric biocontinuous nanostructures in simple aqueous solutions without the need for additives or complex block copolymer architectures (e.g. dendritic-linear, multiblock and miktoarm stars). Switching the solvent to dimethylformamide ($\delta = 24.8$ MPa$^{1/2}$) resulted in the formation of micelles from copolymer 4†, which was initially found to assemble vesicles when THF was instead used as the common solvent (FIG. 3A, Table 1). This result would be expected due to the lower similarity in solubility parameters between DMF and PPS relative to THF and PPS, which would lower chain flexibility and produce slower kinetics for nanostructure transitions. Slowing the transition kinetics through the use of less similar common solvents is known to promote micelle instead of vesicle formation for other block copolymer systems. DLS and cryoTEM revealed copolymer 5 to form micelles even though its fPEG was within the polymersome-forming range (FIG. 8A). This discrepancy can be explained by the higher molecular weight (MW) of the PEG block (MW 2000) relative to the other polymersome forming copolymers (MW 750) (Table 1), as PEG steric stabilization increases with MW and strongly impacts nanostructure morphology. Additionally, the longer PPS chain could result in higher degrees of entanglement and therefore decreased mobility. Copolymer 9 successfully loaded calcein, but had a diameter closer to that of micelles. CryoTEM found this sample to be a mix of morphologies, that included a low percentage of polymersomes and a dominant micelle population (FIG. 8B).

Figures 10A, 10B, 10C, 10D, 10E:
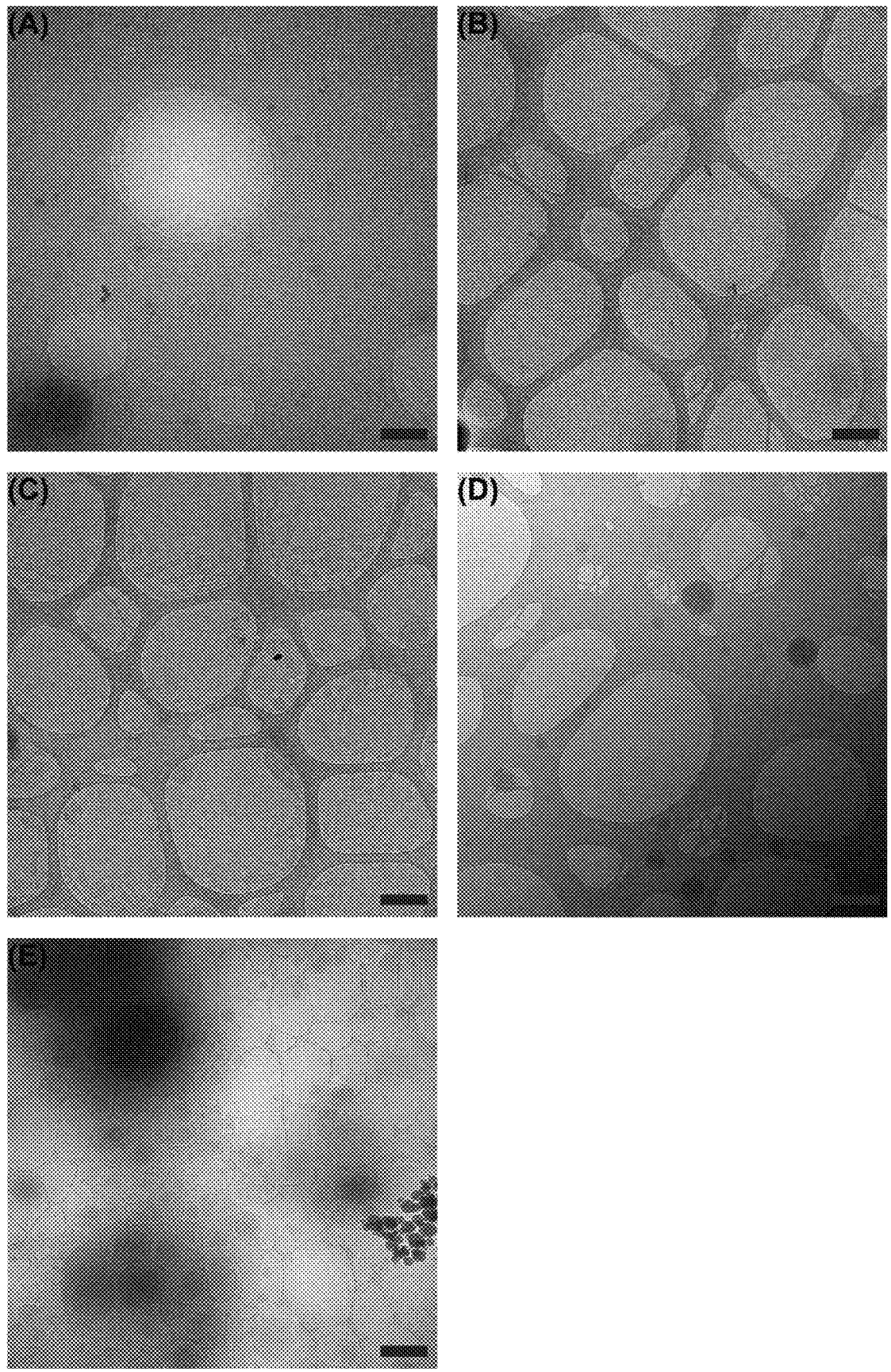
FIGS. 10A-10E show low magnification cryoTEM images of nanostructures formed by FNP. (A) Polymersomes, (B) filomicelles, (C) tubular polymersomes, (D) bicontinuous nanospheres, and (E) multilamellar polymersomes. Scale bar represents 500 nm, except for in (E), where it represents 1500 nm.

The alternative vesicular morphologies of multilamellar and tubular polymersomes (FIGS. 3 and 10A-10A) were detected that were capable of loading calcein in addition to single-bilayered polymersomes. The multilamellar polymersomes represented >30% of assembled nanostructures formed from copolymers 3, 4, 6, 7, and 8 after 2× impingements (FIGS. 3E and 10E and Table 1). These vesicles were easily distinguishable from the relatively common polymersome-within-polymersome structure, as they were characterized by numerous layers of nested vesicles, often reaching a dozen or more layers deep. Although initially absent, tubular polymers with lengths commonly exceeding a micron became a dominant population (>50% of assembled aggregates) after 3× impingements of copolymers 3, 4 and 6 (FIG. 3B, and Table 1). Tubular polymersome are difficult to assemble either quickly or as the dominant aggregate population, often requiring weeks to form and subsequent separation from more prevalent spherical polymersomes.

Figures 4A, 4B, 4C, 4D:
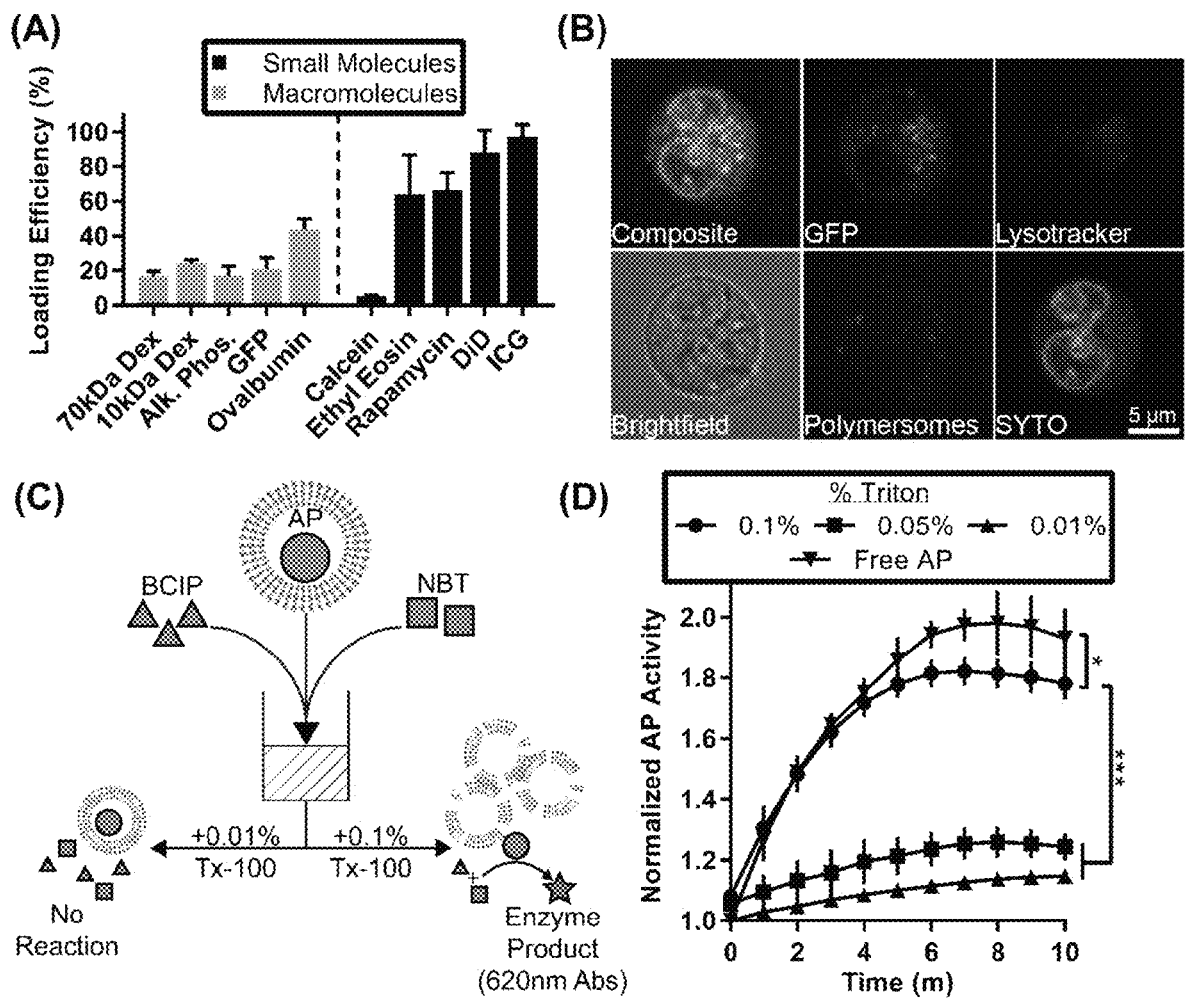
FIGS. 4A-4D show loading of polymersomes with small molecules and macromolecules. (A) Loading efficiency of small molecules and macromolecules. (B) Live-cell confocal microscopy image of polymersome uptake and delivery of GFP in a bone marrow-derived dendritic cell. Polymersomes were loaded with the hydrophobic ethyl eosin (red) and hydrophilic GFP (green). Cells were additionally stained with SYTO 61 (yellow) and lysotracker (blue). Scale bar=5 microns. (C) Graphical representation of experimental setup. Alkaline phosphatase (AP) is represented by circles, BCIP by triangles, and NBT by squares. The product of the enzymatic reaction, formazan, absorbs strongly at 620 nm and is represented by a star. (D) Time-course of enzyme activity assay. Y-axis represents fold increase over original absorbance reading. Error bars represent standard deviation, n=4. Statistical significance determined by 2-way ANOVA, * $p<0.05$ and *** $p<0.001$.

Polymersomes Formed Via Flash Nanoprecipitation Effectively Load Both Hydrophobic and Hydrophilic Molecules A significant benefit of polymersomes over micelles and other lipophilic-core nanoparticles is that their aqueous lumen can encapsulate hydrophilic molecules while hydrophobic molecules can be simultaneously loaded within the vesicle bilayer. FNP has primarily been limited to the encapsulation of hydrophobic molecules with a preferred log P greater than 6 for stable nanoparticle formation. Ion-pairing of weakly hydrophobic and hydrophilic payloads with counter-ions to form hydrophobic salts for complexation with the block copolymer can allow nanoparticle assembly, but this method is not amenable to the loading of most hydrophilic biologics. To determine the influence of payload size and water solubility on loading efficiency into polymersomes, we tested molecules ranging from <1 kDa to >100 kDa and with varying hydrophobicity and Stokes radius: calcein, ethyl eosin, indocyanine green, dextran (10 and 70 kDa), green fluorescent protein (GFP), and alkaline phosphatase (FIG. 4A). With a log P of 1.6, calcein is relatively hydrophilic and small, resulting in the lowest loading efficiency possibly due to its diffusion from the interior of assembling polymersomes into the exterior aqueous reservoir before vesicle stabilization. In contrast, both ethyl eosin and indocyanine green presented very high loading efficiencies, as they can partition into the hydrophobic bilayers during polymersome assembly. The loading efficiency of water soluble macromolecules was significantly higher than for calcein and ranged between 15-25% (FIG. 4A). A number of other variables besides the Stokes radius contribute to the ability for a molecule to permeate through an amphiphilic membrane, including molecular shape, hydrophobic affinity, and membrane thickness. All the macromolecules investigated were hydrophilic, and may have had higher loading efficiencies than calcein due to their size; as the larger macromolecules may have become trapped within the nascent polymersomes during the formation process. This effective encapsulation of macromolecules is important for biomedical applications of polymersomes, as many hydrophilic molecules of interest are macromolecules, such as nucleic acids, peptides, and proteins. Co-loading of hydrophilic and hydrophobic molecules into polymersomes was achieved simply by dissolving water soluble molecules in the aqueous stream and lipophilic molecules in the organic stream prior to impingement within the mixer. The co-loading efficiencies for hydrophilic-hydrophobic pairs of molecules are displayed in Table 2. Encapsulation of calcein (490 nm excitation) and DiI (540 nm excitation) respectively within the polymersome lumen and membrane produced a FRET emission from DiI when exposed to a 490 nm light source (FIG. 10A-10E). The ease of this co-loading process demonstrates that FNP is a powerful tool for the formation of nanocarriers loaded with diverse molecular payloads.

TABLE 2

Loading efficiency for dual-loading by flash nanoprecipitation. All samples fabricated in triplicate. LogP values given when available.

| Dual Loaded Cargoes | Hydrophilic Loading (%) | Hydrophobic Loading (%) | logP Values |
|---|---|---|---|
| TMR-Dextran 70 kDa, ICG | 16.60 ± 2.98 | 97.12 ± 7.04 | N/A, 9.056 |
| Alkaline Phosphatase, Ethyl Eosin | 19.00 ± 5.62 | 64.91 ± 5.42 | N/A, 7.497 |
| Calcein, Ethyl Eosin | 5.06 ± 1.66 | 52.02 ± 2.65 | 1.608, 7.497 |
| Calcein, DiI | 2.54 ± 2.17 | 103.47 ± 12.11 | 1.608, 18.824 |
| GFP, Ethyl Eosin | 20.85 ± 6.74 | 63.71 ± 8.42 | N/A, 7.497 |
| Rapamycin, DiD | N/A | 65.59 ± 7.21 87.88 ± 13.11 | 6.181, 19.38 |

TABLE 3

Loading efficiency for DNA molecules by flash nanoprecipitation.

| Polymer | Size | PDI | Zeta potential | % loading |
|---|---|---|---|---|
| NH2-PEG1K-PPS82 | 94 ± 1 | 0.19 ± 0.03 | 42 ± 3.8 | NA |
| 50 µg DNA loaded | 101.8 ± 1 | 0.21 ± 0.01 | 30.1 ± 1.2 | 70 |
| 0.5 µg DNA loaded | 114.6 ± 2.6 | 0.18 ± 0.02 | 39.9 ± 5.3 | NA |
| 50 µg DNA in PEK17-PPS35 | 213.9 ± 7.9 | 0.43 ± 0.01 | 0.56 ± 0.26 | 30 |

TABLE 4

Positively charged amine-functionalized polymers designed to enhance DNA loading.

| Polymer | Size | PDI | Zeta potential |
|---|---|---|---|
| NH2-PEG1K-PPS82 Water | 98 ± 1 | 0.17 ± 0.06 | 44 ± 1 |
| NH2-PEG1K-PPS82 PBS | 94 ± 1 | 0.19 ± 0.03 | 42 ± 1 |

Alkaline Phosphatase Remains Enzymatically Active Following Loading within Polymersomes Via Flash Nanoprecipitation One concern for the use of FNP with proteins is the mixing of organic solvent with the aqueous solution, which has the potential to denature the structure of proteins and decrease their bioactivity. A possible solution to this concern is to load the hydrophilic cargo within the reservoir, after the impingement has occurred but before the vesicles have fully assembled. To determine the efficiency of this method, we attempted to simultaneously load polymersomes with two separate fluorescent dextrans of the same molecular weight by dissolving one in the impinged aqueous stream and one in the reservoir at the same concentration. The highly water soluble macromolecule dextran (10 kDa) tagged with either cascade blue (CB) or fluorescein (F) was used. To avoid any potential influences of the attached fluorophore on the loading efficiency, we conducted the experiments in pairs, with the dextran-CB in the syringe and dextran-F in the reservoir, and vice versa. We found there to be a statistically significant increase in loading via syringe compared to reservoir, though loading by reservoir still occurred at detectable levels (FIG. 6A). We further investigated whether loading via reservoir or syringe resulted in a greater amount of functional protein by loading GFP, which has a conformation-dependent fluorescence. We found that GFP fluoresced at equal levels whether loaded by syringe or reservoir (FIG. 6B).

Figure 11:
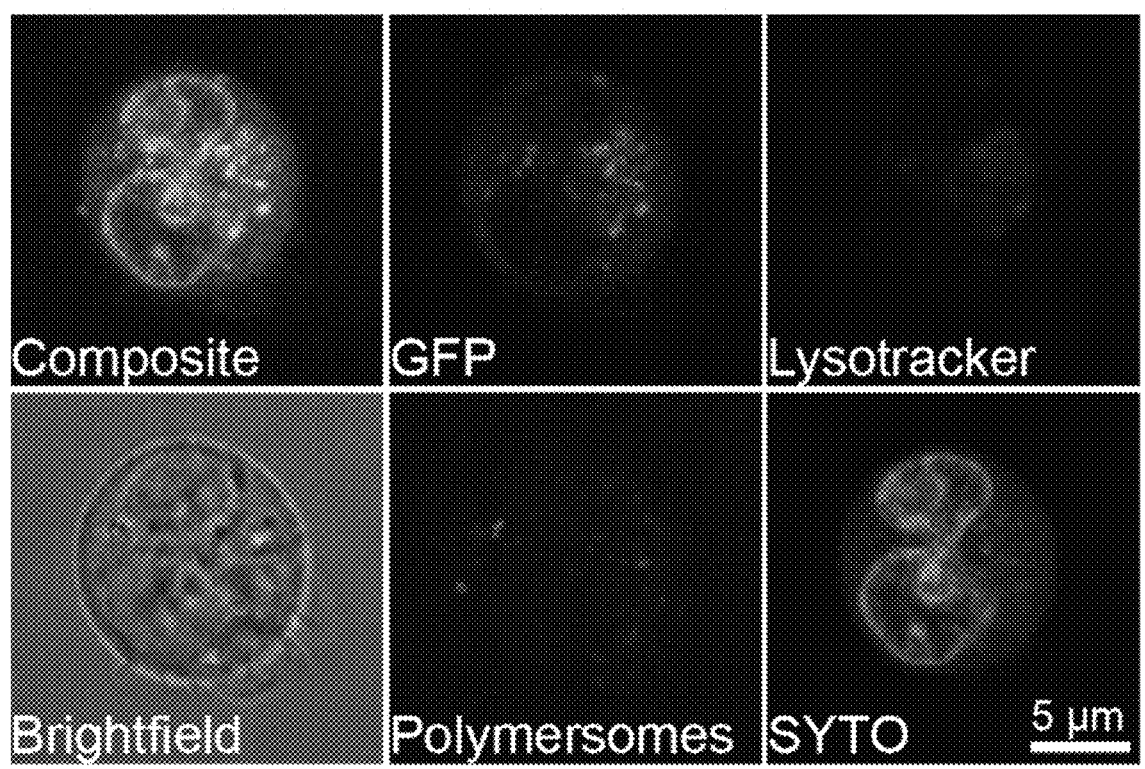
FIG. 11 shows live-cell confocal microscopy image of polymersome uptake and delivery of GFP in a RAW 264.7 cell. Polymersomes were loaded with the hydrophobic ethyl eosin (red) and hydrophilic GFP (green). Cells were additionally stained with SYTO (yellow) and lysotracker (blue). Scale bar=5 microns.
Figures 12A, 12B, 12C, 12D, 12E, 12F, 12G, 12H:
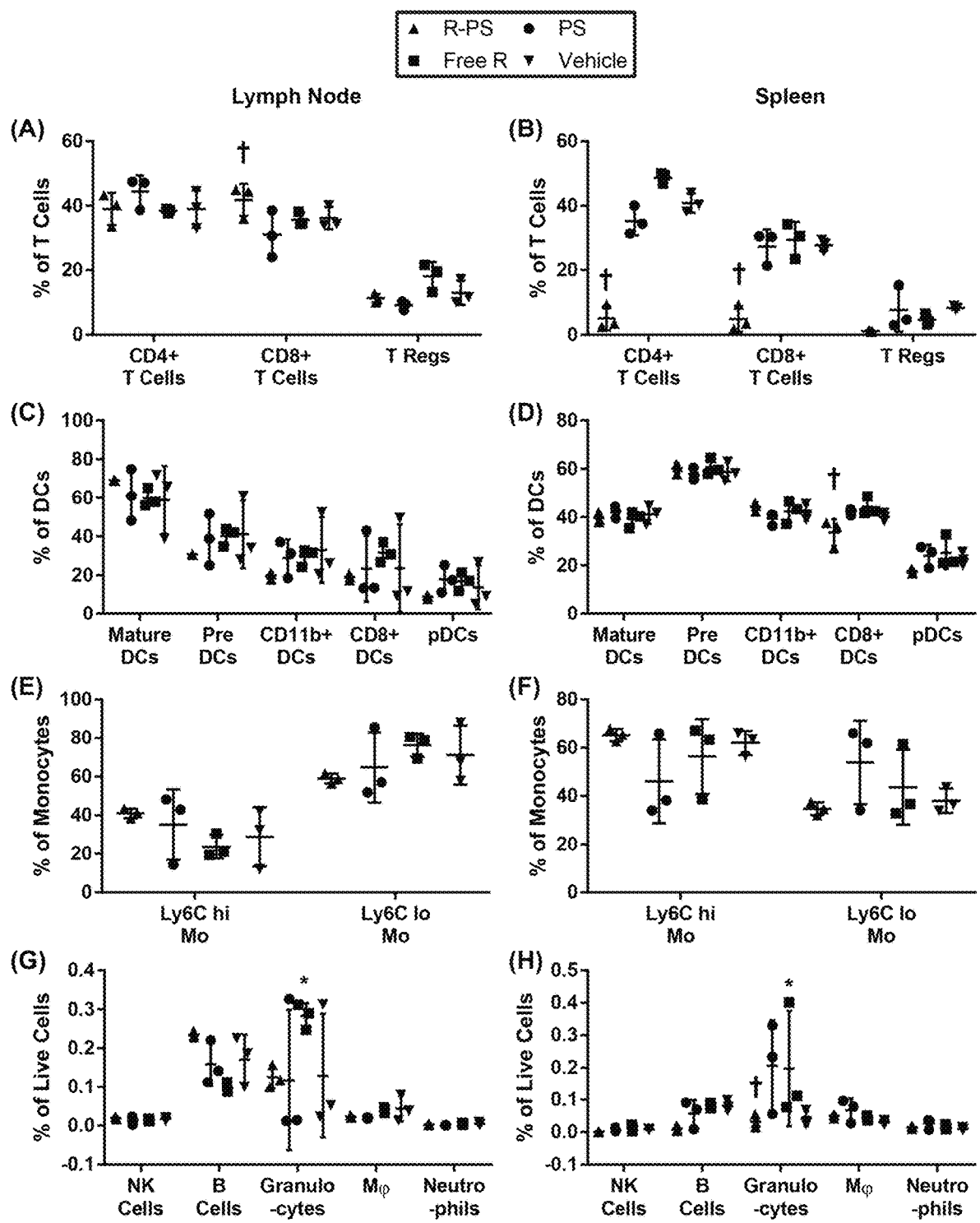
FIGS. 12A-12H show percentages of total live cells in the lymph nodes (FIGS. 12A, 12C, 12E, 12G) and spleen (FIGS. 12B, 12D, 12F, 12H) that are T cells, dendritic cells (DCs), plasmacytoid dendritic cells monocytes (Mo), B cells, granulocytes, macrophages (My), and neutrophils. † indicates rapamycin polymersome treated populations that were significantly altered compared to blank polymersomes. * indicates free rapamycin treated populations that were significantly altered compared to vehicle.

The activity of GFP in biologically-relevant systems was further explored by delivering GFP in vitro within polymersomes to bone marrow-derived dendritic cells (BMDCs). BMDCs were generated from bone marrow freshly collected from C57BL/6 mice, and after maturation were plated in the presence of polymersomes. The polymersomes were co-loaded with the hydrophobic dye ethyl eosin and hydrophilic GFP, and the cells were further stained with nuclear stain SYTO 61 and lysosome stain Lysotracker Blue prior to imaging on a confocal microscope. Punctae of GFP and ethyl eosin were found within cells, demonstrating that conformationally-active GFP could be delivered to live cells via polymersomes (FIG. 11). These results supported previously published confocal microscopy images and verifies that FNP had no impact on the ability of PEG-bl-PPS polymersomes to deliver payloads to the cytoplasm of BMDCs.

To further confirm the continued biological activity of loaded proteins, we investigated the function of an enzyme, alkaline phosphatase (AP), encapsulated into polymersomes by FNP. AP removes phosphate groups from a number of substrates, including 5-bromo-4-chloro-3-indolyl-phosphate (BCIP), whose dephosphorylation is detectable by nitro blue tetrazolium (NBT) at an absorbance of 620 nm. We therefore encapsulated AP into the lumen of polymersomes using FNP, and added them to a solution of BCIP and NBT (FIG. 4B). AP-polymersomes were lysed using Triton X-100 to allow the AP, BCIP and NBT to freely react in solution (FIG. 4C). At low concentrations of Triton X-100 a low level of background reactivity was observed in the system, which was likely due to a burst effect resulting from the release of hydrophilic reagents trapped within the vesicle membranes. The addition of 0.1% Triton X-100 resulted in the continued formation of significantly more product over a ten-minute period, verifying the retention of AP tertiary conformation and bioactivity following encapsulation within polymersomes by FNP (FIG. 4C).

Low Dosage Subcutaneous Administration of Rapamycin Loaded into Polymersomes by Flash Nanoprecipitation Reduces Splenic CD4+ and CD8+ T Cell Populations in Mice To explore FNP as a method to fabricate polymersome formulations for the in vivo delivery of therapeutics, we loaded the model immunomodulatory drug rapamycin (Sirolimus), an FDA-approved immunomodulator, into fluorescent polymersomes. Rapamycin has a low water solubility (log P=6.181) and loaded readily into polymersomes with an efficiency of 65% (FIG. 4A). Rapamycin inhibits the mechanistic target of rapamycin (mTOR) kinase, which is a key regulator of cell growth, metabolism and proliferation and elicits cellular responses that are highly dependent on the cell type. Thus, identifying which cells are being influence by rapamycin is critical to understanding immune responses generated during its therapeutic use, and this may be achieved via an immunotheranostic delivery system. In the case of T cells, mTOR inhibition is known to decrease proliferation, migration and overall population levels for T cells, particularly CD4+CD25− T cell and effector CD8+ T cell subsets. For dendritic cells, rapamycin has a suppressive effect on maturation and differentiation by inhibiting expression of co-stimulatory molecules and inflammatory cytokines. Macrophages respond to rapamycin by polarizing towards a pro-inflammatory M1 phenotype. Although T cells are not phagocytic and do not associate with polymersomes, their levels and activity can be modulated via the targeting of antigen presenting cells, such as phagocytic macrophages and dendritic cells. PEG-bl-PPS nanocarriers are endocytosed by phagocytic immune cells in lymph nodes and spleen following SC administration, and we hypothesized that controlled delivery of rapamycin within polymersomes to these cells may enhance immunosuppression at lower dosages than what is typically employed therapeutically in mice while avoiding uptake of rapamycin by T cells. Rapamycin is administered to mice orally, intraperitoneally, and subcutaneously, at doses ranging from 75 µg/kg/day to >10 mg/kg/day. Generally, an effective dose for sustained allograft survival in mice is considered to be 1.5-3 mg/kg/day.

Figures 5A, 5B, 5C, 5D:
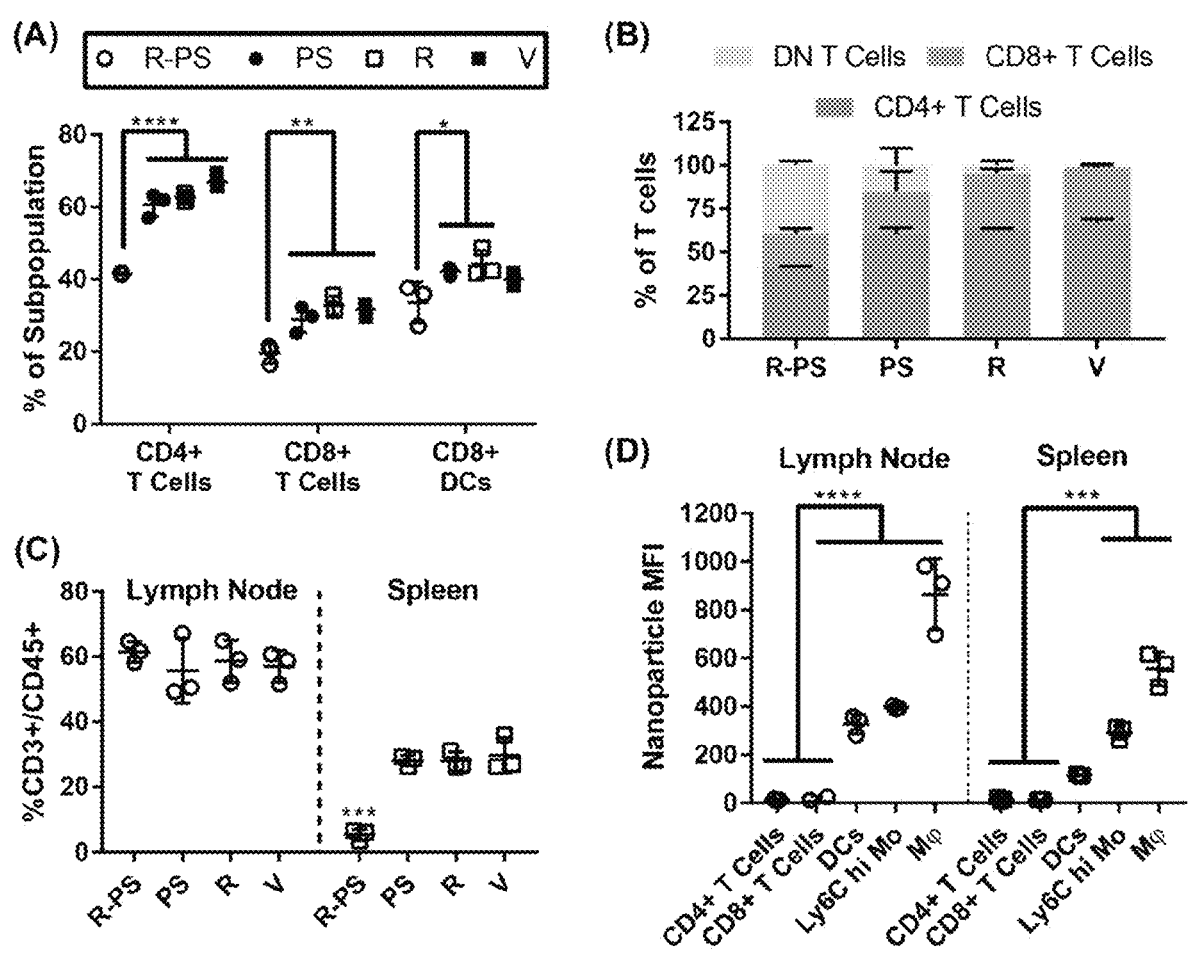
FIGS. 5A-5D show in vivo delivery of theranostic rapamycin/DiD-loaded polymersomes formed by flash nanoprecipitation.
Figure 13:
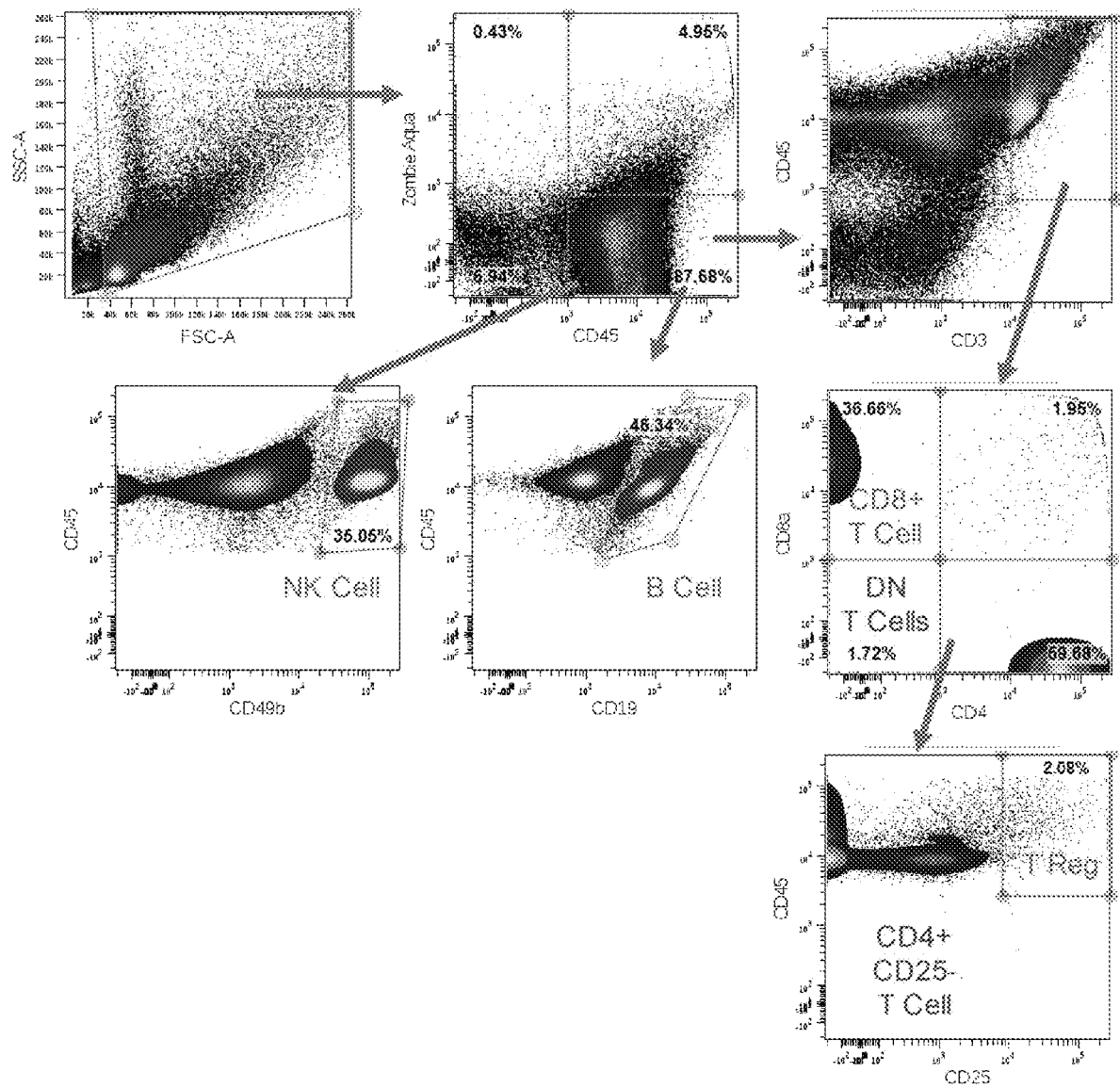
FIG. 13 depicts gating strategy for immune cells isolated from mouse spleen to identify natural killer (NK) cells, B cells, CD4+ T cells, CD8+ T cells, 'double negative' (DN) T cells, and regulatory T cells (T Reg). All plots shown are representative gating strategies for cells, in this case from the spleen of a vehicle treated mouse.
Figure 14:
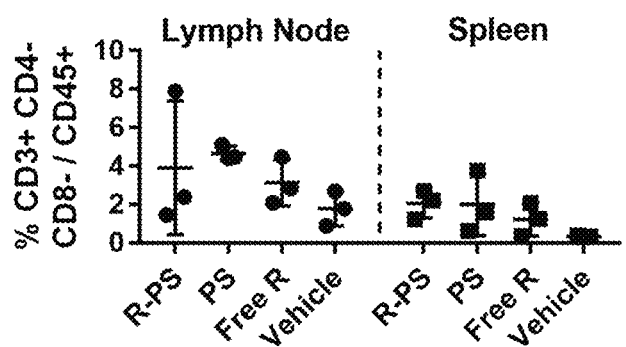
FIG. 14 shows percentage of DN T cells within the CD45+ cell population in the lymph nodes and spleen. N=3.
Figure 15:
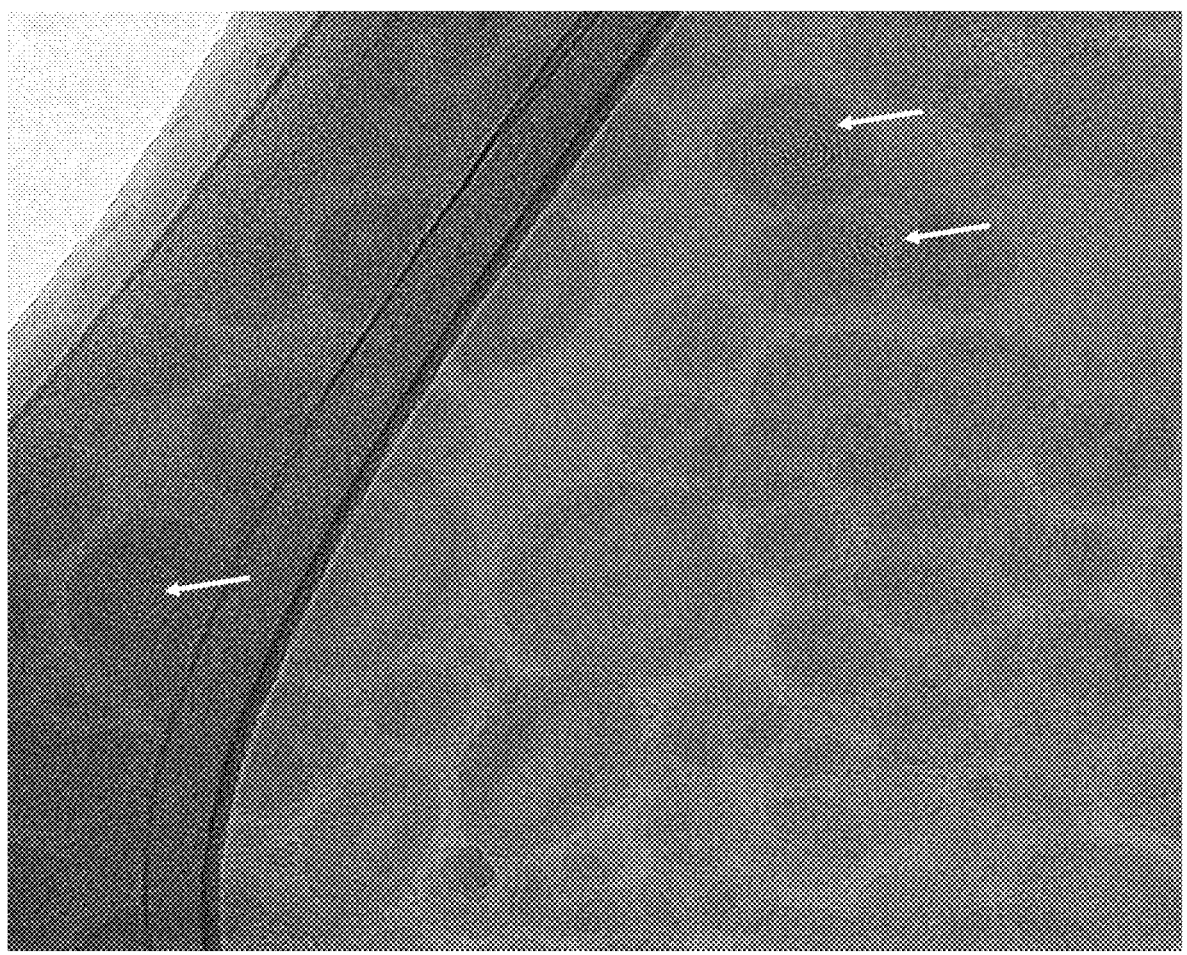
FIG. 15 shows cryoTEM images of loading of DNA into nanocarrier architectures. The rope-like structures within the vesicles shows loaded DNA.
Figure 16:
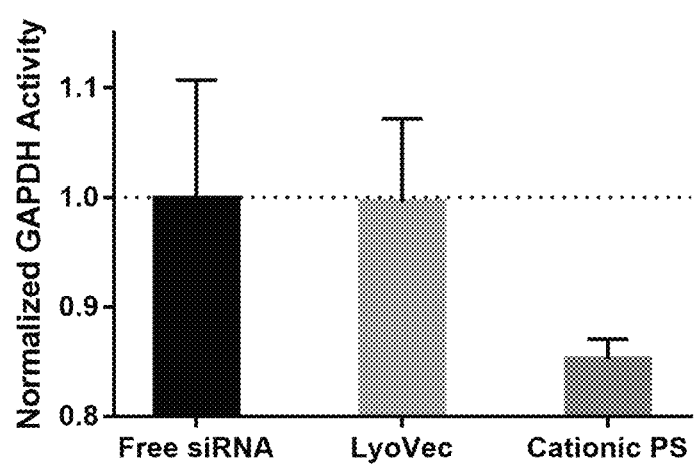
FIG. 16 shows a comparison of the knockdown efficiency of siRNA-loaded polymersomes compared to a commercially available gene delivery platform. LyoVec is the commercial gene delivery platform and cationic PS are polymersomes composed of copolymers that were end-functionalized with amines to give them a positive charge for better association with nucleic acids. Loaded siRNA was specific for glyceraldehyde 3-phosphate dehydrogenase (GSPDH).

To demonstrate the difference between rapamycin efficacy in its polymersome-loaded versus free form, we administered rapamycin to mice once every three days at an effective average dosage of only 0.33 mg/kg/day. After only three administrations of rapamycin loaded polymersomes, we found that splenic CD4+ and CD8+ T cells were significantly reduced in proportion to the total number of T cells compared to free rapamycin, which instead elicited no significant effects on T cells (FIGS. 5A, 12A-12H, and flow cytometry gating strategy shown in FIG. 13). CD8+ dendritic cells, a dendritic cell population known for superior cross presentation of antigen and resulting CD8+ T cell activation, were also significantly decreased in proportion to the total number of dendritic cells (FIGS. 5A, 12A-12H). The significant drop in CD4+ T cells and CD8+ T cells was accompanied by an increase in the proportion of 'double negative' (CD4− CD8−, DN) T cells (FIG. 5B) and a decrease in the total number of T cells (FIG. 5C). The increase in the proportion of DN T cells was matched by the overall decrease in T cells, resulting in no significant change in the proportion of DN T cells within the total immune cell population (FIG. 14). Although rapamycin has been employed for in vitro and in vivo expansion of regulatory T cells (Tregs) in mice, we found no significant changes in Treg levels following controlled delivery within polymersomes. Free rapamycin was found to have no significant impact on any immune cell populations at this comparatively low dosage and brief course of treatment (FIGS. 5, 12A-12H). The decrease in CD4+ and CD8+ T cell populations is not likely to have occurred through direct intracellular delivery of rapamycin to T cells, as these cells showed no association with polymersomes as measured by DiD fluorescence (FIG. 5D). In contrast, phagocytic cells in both the lymph nodes and spleen, such as macrophages, Ly-6C$^{hi}$ monocytes, and dendritic cells all demonstrated significant uptake of polymersomes (FIG. 5D). Modulation of Treg levels for T cell suppression in mice via rapamycin has been found to require 1.5 mg/kg/day for 14 days or 3 mg/kg/day for 4 days in a separate study, thus it is not surprising that we observed no changes in Treg levels at a dosage of only 0.33 mg/kg/day over the course of 1 week. This theranostic strategy thus implicates antigen presenting cells as the mediators of our observed rapid low-dosage T cell immunosuppression, and demonstrates that flash nanoprecipitation can be employed for the fabrication and loading of soft nanoarchitectures capable of controlled dual delivery of imaging agents and therapeutic drugs in vivo.

Conclusion

Delivery of drugs in vivo, ranging from hydrophilic to hydrophobic and small molecule to protein biologics, remains a significant challenge for the field of biomedical research. Concerns over efficiency, stability, and scalability have plagued many fabrication processes for self-assembled soft nanoarchitectures, many of which hold vast and unrealized potential for advanced strategies of controlled delivery. Here, we have demonstrated that FNP, a rapid and scalable method of assembling solid-core block copolymer nanoparticles, can be used to assemble PEG-bl-PPS into monodisperse polymersomes and a variety of other soft nanoarchitectures, including tubular and multilamellar polymersomes, filomicelles and rare polymeric bicontinuous nanospheres. FNP is usually performed using block copolymers with high Tg hydrophobic blocks, like polystyrene, that undergo slow structural transitions and allow the formation of stable micellar aggregates. The present results suggest that matching the copolymer aggregation rate with the turbulent mixing time during FNP, which can be controlled by the flow rate through the mixing chamber, may allow FNP to be applied for the formation of diverse metastable nanostructures for other polymers in addition to PEG-bl-PPS. FNP was surprisingly found to be used to effectively load (and co-load) vesicular nanoarchitectures with small molecules and proteins with a wide range of water solubility and molecular weights while maintaining their biological activity. The inventors demonstrated three examples of biological relevance: in vitro delivery of GFP to BMDCs, in vitro enzyme activity of alkaline phosphatase, and in vivo delivery of rapamycin to immune cells, the latter of which demonstrated immunosuppression of CD4+ and CD8+ T cells at a 5-fold lower dosage than is typically utilized. These findings significantly expand the capabilities of FNP and provide new routes for the high throughput nanofabrication of diverse therapeutic nanocarriers.

Materials and Methods

Materials

The following reagents were obtained from Sigma-Aldrich: poly(ethylene glycol) methyl ether MW 2000 (product 202509), poly(ethylene glycol) methyl ether MW 750 (product 202495), poly(ethylene glycol) MW 300 (product 202371), methanesulfonyl chloride (product 471259), triethylamine (product T0886), potassium carbonate (product 791776), thioacetic acid (product T30805), 0.5M sodium methoxide solution (product 403067), propylene sulfide (product P53209), acetic acid (product 695092), benzyl bromide (product B17905), N-(2-bromoethyl)phthalimide (product B66302), 2,2'-dipyridyl disulfide (product 143049), calcein (product C0875), ethyl eosin (product 199540), indocyanine green (product 12633), dichloromethane (product 320269), celite filter cel (product 22139), activated charcoal powder (product 161551), anhydrous tetrahydrofuran (product 401757), tetrahydrofuran (product 437638), ethanol (product 459844), methanol (product 179337), diethyl ether (product 346136), deuterated chloroform (product 151823), Tween 80 (product P8074), and sepharose 4B (product 4B200). The following reagents were purchased from ThermoFisher Scientific: tetramethylrhodamine-dextran 70 kDa (product D1818), fluorescein-dextran 10 kDa (product D1820), cascade blue-dextran 10 kDa (product D1976), DiI (product V22885), DiD (product D7757) toluene (product T324), hexanes (product H292), HPLC-grade dimethylformamide (product AA22915K2), Lysotracker Blue DND-22 (product L7525), SYTO 61 (product S11343), ACK lysing buffer (product A1049201), HBSS (product 14175079) and 1×PBS tablets (product BP2944). Recombinant A. victoria GFP protein was a generous gift from the Jewett Lab at Northwestern University. Electron microscopy holey carbon 200 mesh copper grids were purchased from Electron Microscopy Sciences (product HC200CU). Rapamycin was purchased from Selleck Chemicals. Recombinant IL-4, recombinant GM-CSF, and all antibodies for flow cytometry were purchased from BioLegend.

Polymer Synthesis

The synthesis of poly(ethylene glycol)-block-poly(propylene sulfide) (PEG-bl-PPS) was performed as described previously. Briefly, methyl ether PEG (MW 750 and 2000) were functionalized first with the mesylate leaving group, which was then reacted with thioacetic acid to form a protected PEG-thioacetate. Base activation of the thioacetate resulted in the formation of a thiolate anion, which was used as the initiator for ring opening polymerization of propylene sulfide. The reaction was completed with the addition of end capping groups (benzyl bromide or bromoethyl phthalimide), a disulfide-bonding group (dipyridyl disulfide), or the protonation of the thiolate anion with acetic acid, leaving a free thiol at the end of the polymer (PEG-bl-PPS-thiol). Degree of polymerization was assessed via H1 NMR (3H methyl ether, 3.36 singlet; 4H PEG —$CH_2$—$CH_2$—, wide peak 3.60-3.64; 1H $CH_2$—CH—$CH_3$ wide peak 2.56-2.65; 2H—CH—$CH_2$—CH—$CH_3$, wide peak 2.82-2.95, 3H—$CH_2$—$CH_3$ wide peak 1.30-1.38).

Nanocarrier Fabrication Via Flash Nanoprecipitation

Nanocarriers were formed using the confined impingement jets (CIJ) mixer described by Han et al. PEG-bl-PPS copolymers and hydrophobic molecules to be loaded within polymersomes were dissolved in 500 µL of tetrahydrofuran (THF) and placed into a 1 mL plastic disposable syringe. 500 µL of phosphate buffered saline (1×PBS) and any hydrophilic molecules to be loaded within the vesicle lumen were prepared in a second 1 mL syringe. The two solutions were impinged against one another within the CIJ mixer by hand, at a rate of approximately 1 mL/s. The supersaturated solution exited the mixer into a 20 mL glass scintillation vial containing a 2.5 mL reservoir of 1×PBS. This product was then separated from unloaded molecules and THF on a sepharose 4B size exclusion column. For fluorescence measurements, samples were taken both before and after column purification to assess loading efficiency.

Alternative Nanocarrier Fabrication Techniques

As controls, polymersomes were formed by the standard solvent dispersion and thin film techniques. In the case of solvent dispersion, 20 mg of polymer was dissolved in 500 µL of THF, which was dripped into a stirring reservoir of 3 mL of 1×PBS. This resulted in an identical THF:1×PBS ratio as used for the FNP fabrication method. Hydrophobic molecules were dissolved in the requisite organic solvent and added to the polymer/THF solution prior to addition to 1×PBS. Hydrophilic molecules were first dissolved in the 1×PBS reservoir prior to the addition of the polymer/THF solution. In the case of thin film, 20 mg of polymer was weighed into a 1.8 mL glass HPLC vial and dissolved in 750 µL of DCM, which was subsequently removed by vacuum desiccation for 6 hours. 1 mL of 1×PBS was then added to the HPLC vial, which was shaken at 1500 rpm overnight on a Multi-Therm shaker (Heidolph) at room temperature. Hydrophobic molecules, dissolved in their respective organic solvent, were added to the polymer/DCM solution, and were dried with the polymer in the vacuum desiccator. Hydrophilic molecules were dissolved first in the 1×PBS prior to its addition to the dried polymer deposit for hydration under shaking at room temperature.

Co-Loading Experiments

For calcein and ethyl eosin co-loading experiments, the aqueous solvent consisted of 0.4 mM calcein in 1×PBS. 10 µL of a 5 mg/mL ethyl eosin solution in ethanol was added to 490 µL of THF and 20 mg of polymer. For the TMR-dextran and ICG co-loading experiments, 2 mg of TMR-dextran (70 kDa) was dissolved in 500 µL 1×PBS. 50 µL of a 1 mg/mL ICG solution in ethanol was added to 450 µL of THF and 20 mg of polymer. For alkaline phosphatase-ethyl eosin co-loading experiments, alkaline phosphatase was loaded at a concentration of 1 mg/mL within the reservoir, while 10 µL of a 5 mg/mL ethyl eosin solution in ethanol was added to 490 µL of THF and 20 mg of polymer. For calcein and DiI co-loading experiments, the aqueous solvent consisted of a 0.4 mM calcein solution in 1×PBS, which was impinged against 490 µL THF with 10 µL DiI (as supplied) and 20 mg of polymer. For the experiments examining the relative loading of fluorescein-dextran and cascade blue-dextran, both were used from stock solutions of 1 mg/mL in 1×PBS. For the GFP loading experiments, 50 µL of a 200 µg/mL was dissolved in 450 µL of 1×PBS (for syringe loading) or 2.45 mL 1×PBS (for reservoir loading), while 20 mg of polymer was dissolved in 500 µL of THF.

Multiple Impingement Experiments

For the multiple impingement samples, the organic and aqueous impingement solutions were prepared as previously described for the calcein/ethyl eosin co-loading experiments with a few exceptions. In this case, rather than containing 2.5 mL of 1×PBS, the scintillation vial reservoir was initially empty. Following each impingement, the resulting solution containing 1:1 THF:1×PBS, 20 mg of polymer, calcein, and ethyl eosin, was split evenly into two 1 mL syringes, and reintroduced into the CIJ mixer. This process was repeated between one and four times, with the final impingement emptying into a reservoir containing 2.5 mL of 1×PBS.

Spectrometric Fluorescence and Absorbance Measurements

Fluorescence and absorbance measurements were taken on a SpectraMax M3 microplate reader (Molecular Devices). All readings were taken in black-walled clear bottom 96-well plates (Corning 07-200-567), at 100 µL volumes. All readings were normalized to a 100 µL 1×PBS blank control. The following settings were used for fluorescence measurements for each fluorophore (excitation/emission, filter used): calcein: 470/509, 495 filter), ethyl eosin: 525/560, 550 filter, tetramethylrhodamine: 555/580, 570 filter, fluorescein: 494/524, 515 filter, cascade blue: 400/420, 420 filter, indocyanine green: 780/820, no filter, DiI: 549/565, 550 filter, DiD: 644/670, 665 filter and GFP: 485/535, 495 filter. NBT diformazan was detected via absorbance at 620 nm.

Rapamycin Loading Efficiency by HPLC UV Absorbance

50 µL aliquots of formulations containing rapamycin were frozen at −80 C for at least 3 hours, then were lyophilized overnight. Lyophilized samples were dissolved in HPLC grade DMF and were vortexed then briefly centrifuged to pellet salt from the formulation. Samples were run on a Thermo Fisher Dionex UltiMate 3000 system with an Agilent Polypore 7.5×300 mm column with an Agilent Polypore 7.5×50 mm guard column, housed at 60 C. The organic mobile phase was HPLC grade DMF, run at 0.5 mL/min. Rapamycin was detected using UV absorbance at 270 nm. For loading efficiency, aliquots were taken from samples before and after column purification. Analysis was performed using the Thermo Scientific Chromeleon software.

Alkaline Phosphatase Enzyme Activity Assay

Alkaline phosphatase was dissolved at 1 mg/mL in 2.5 mL of 137 mM NaCl solution for the reservoir. Unloaded polymersomes were formed by similarly but without alkaline phosphatase. All polymersome samples were purified by size exclusion chromatography (sepharose 4B) to remove THF and unloaded cargo. A stock solution of premixed NBT and BCIP was used (560 µM BCIP and 480 µM NBT prepared in 10 mM Tris and 59.3 mM $MgCl_2$). 40 µL of polymersomes was added to wells of a 96 well plate, along with 10 uL of NBT/BCIP solution. Cargo release was performed by the addition of 50 µL of Triton X-100 solution, with final concentrations of Triton X-100 of 0.1%, 0.05%, and 0.01%. Absorbance measurements were taken every two minutes for 10 minutes.

Size Measurements

Hydrodynamic diameters of nanostructures were measured using nanoparticle tracking analysis (NTA) on a Nanosight NS300 (Malvern). Measurements were taken using samples at a 1:1000 dilution in 1×PBS, resulting in approximately 0.1 mg/mL polymer concentrations. Readings were performed using a 633 nm laser. Five 1 minute videos were recorded per sample, with results averaged across the five readings. For micellar samples, typically >20 nm in diameter, dynamic light scattering measurements were performed using a Zetasizer (Malvern) to more accurately measure the size distribution, due to the limitations of NTA for smaller diameter aggregates.

Log P Values

Log P values were pulled from the ZINC15 database (zinc15.docking.org).

Cryogenic Transmission Electron Microscopy

Specimens for cryoTEM were prepared by applying 4 µL of 1 mg/ml sample on a pretreated, holey carbon 400 mesh TEM grids and were plunge-frozen with a Gatan Cryoplunge freezer. Images were collected in vitreous ice using a JEOL 3200FSC transmission electron microscope operating at 300 keV at 4,000× nominal magnification. A total dose of ~10 $e^-/Å^2$ and a nominal defocus range of 2.0-5.0 µm were used. Micrographs were acquired using a Gatan 3.710×3,838 pixel K2 Summit direct electron detector operating in counting mode. Each micrograph was acquired as 20-frame movies during a 5 s exposure. After data acquisition, the individual frames of each micrograph were aligned using Digital Micrograph software (Gatan) to compensate for stage and beam-induced drift, and the aligned images were summed for further image processing.

Animals

C57BL/6 male mice, 6-8 weeks old, were purchased from Jackson Labs. All mice were housed and maintained in the Center for Comparative Medicine at Northwestern University. All animal experimental procedures were performed according to protocols approved by the Northwestern University Institutional Animal Care and Use Committee (IACUC).

Live-Cell Confocal Microscopy

Bone marrow derived dendritic cells were generated from bone marrow collected from the tibias and femurs of C57BL/6 mice, in a protocol slightly modified from those described previously. Tibias and femurs of C57BL/6 mice were cleaned of tissue, cut, and flushed through with 10% FBS in HBSS. Cells were centrifuged, supernatant was removed, and they were then treated with ACK lysis buffer for 5 minutes. Lysis was stopped with the addition of excess HBSS, and cells were centrifuged again, resuspended in 10 mL 10% FBS 1× Penstrep RPMI, and were plated in 100 mm petri dishes. Every three days, 200 ng of GM-CSF and 100 ng of IL-4 were added to culture. On the $8^{th}$ day of maturation, cells were collected and plated into a FluoroDish at $3\times10^5$ cells/mL, along with 15 uL of dual-loaded GFP ethyl eosin polymersomes. Lysotracker Blue (lysosome stain) and SYTO 61 (nuclear stain) were added at 1:10,000 dilutions. Plated cells were imaged within a humidified chamber using a 63× oil-immersion objective on a SP5 Leica Confocal Microscope using HyD detectors and four lasers: 415 nm diode laser for Lysotracker Blue, 488 nm argon laser for GFP, 514 nm argon laser for ethyl eosin, and 633 nm HeNe laser for SYTO 61.

In Vivo Rapamycin Delivery

Formulations of rapamycin polymersomes and blank polymersomes were formed by flash nanoprecipitation using 20 mg of PEG17-bl-PPS36-Thiol polymer, with or without 0.5 mg rapamycin, respectively, dissolved in THF. Sterile 1×PBS was used as the aqueous phase and reservoir solution. Fluorescently labeled polymersomes of both formulations were formed similarly, with the addition of 25 µg of DiD in the organic phase. A formulation of free rapamycin was made in a solution of 8% ethanol, 10% PEG300, and 10% Tween 80 in 1×PBS. Briefly, rapamycin was dissolved in ethanol (3 mg/mL), and 31.2 µL was added to 1 mL of a solution of 10% PEG300 and 10% Tween 80 in 1×PBS (3.1% ethanol final, ~125 µg/mL rapamycin concentration). Vehicle was also injected without rapamycin, in which case 31.2 µL of pure ethanol was added to the 10% PEG300 10% Tween 80 solution. Mice were injected subcutaneously, slightly anterior to the scapula, with 1 mg/kg doses of rapamycin, or equivalent injections of vehicle or blank polymersomes, N=3 per treatment group. Injections were performed on days 1, 4 and 7, with the final set of injections containing fluorescently labeled polymersomes, when applicable. Mice were sacked on day 8, and the draining (brachial) lymph nodes were collected, along with the spleens. Organs were mechanically homogenized in RPMI media and passed through a 70 µm cell strainer before being stained for flow cytometry.

Flow Cytometry

Splenic cells were first treated with ACK lysis buffer for 5 minutes on ice before being spun down and resuspended in blocking buffer. Cells were stained with Zombie Aqua as a fixable live/dead stain and FcRs were blocked with anti-mouse CD16/CD32. Cells were stained with a cocktail of antibodies in three panels. Panel 1: anti-mouse CD45 FITC, anti-mouse CD3 APC-Cy7, anti-mouse CD4 PE-Cy5, anti-mouse CD8a PE-Cy7, anti-mouse CD19 Pacific Blue, anti-mouse CD49b PerCp-Cy5.5, and anti-mouse CD25 PE. Panel 2: anti-mouse CD11b PerCp-Cy5.5, anti-mouse CD11c Pacific Blue, anti-mouse I-A/I-E FITC, anti-mouse B220 PE, anti-mouse Gr-1 APC-Cy7, and anti-mouse CD8a PE-Cy7. Panel 3: anti-mouse CD11b PerCp-Cy5.5, anti-mouse CD11c Pacific Blue, anti-mouse F4/80 FITC, anti-mouse Ly-6C APC-Cy7, and anti-mouse Ly-6G PE-Cy7. After washes, cells were fixed by IC cell fixation buffer (Biosciences). Flow cytometry was performed with FACSDiva on a LSRII flow cytometer (BD Biosciences), with the APC channel used to detect the DiD loaded into polymersomes. Data was analyzed using CytoBank online software.

Statistical Analysis

Statistical significance for changes in nanostructure diameter and polydispersity by multiple impingements and changes in loading efficiency by loading method were determined using Student's t-test, with multiple comparison correction via the Holm-Sidak method, alpha=0.05. All other statistical significance was determined by 2-way ANOVA and Tukey's multiple comparison test, alpha=0.05. In all graphs, *=p<0.05, =p<0.01, *=p<0.001, and ****=p<0.0001. All statistical analysis was performed using GraphPad Prism.

REFERENCES

X. Duan, Y. Li, Physicochemical Characteristics of Nanoparticles Affect Circulation, Biodistribution, Cellular Internalization, and Trafficking, Small 9(9-10) (2013) 1521-1532.

Y. Geng, P. Dalhaimer, S. Cai, R. Tsai, M. Tewari, T. Minko, D. E. Discher, Shape effects of filaments versus spherical particles in flow and drug delivery, Nat Nanotechnol 2(4) (2007) 249-55.

A. Stano, E. A. Scott, K. Y. Dane, M. A. Swartz, J. A. Hubbell, Tunable T cell immunity towards a protein antigen using polymersomes vs. solid-core nanoparticles, Biomaterials 34(17) (2013) 4339-46.

C. H. Choi, L. Hao, S. P. Narayan, E. Auyeung, C. A. Mirkin, Mechanism for the endocytosis of spherical nucleic acid nanoparticle conjugates, Proc Natl Acad Sci USA 110(19) (2013) 7625-30.

T. Wang, J. Bai, X. Jiang, G. U. Nienhaus, Cellular uptake of nanoparticles by membrane penetration: a study combining confocal microscopy with FTIR spectroelectrochemistry, ACS Nano 6(2) (2012) 1251-9.

C. Tang, D. Amin, P. B. Messersmith, J. E. Anthony, R. K. Prud'homme, Polymer directed self-assembly of pH-responsive antioxidant nanoparticles, Langmuir 31(12) (2015) 3612-20.

W. S. Saad, R. K. Prud'homme, Principles of nanoparticle formation by flash nanoprecipitation, Nano Today 11(2) (2016) 212-227.

B. K. Johnson, R. K. Prud'homme, Flash NanoPrecipitation of organic actives and block copolymers using a confined impinging jets mixer, Aust. J. Chem. 56(10) (2003) 1021-1024.

J. Han, Z. Zhu, H. Qian, A. R. Wohl, C. J. Beaman, T. R. Hoye, C. W. Macosko, A simple confined impingement jets mixer for flash nanoprecipitation, J. Pharm. Sci. 101(10) (2012) 4018-23.

J. C. Cheng, R. D. Vigil, R. O. Fox, A competitive aggregation model for Flash NanoPrecipitation, J. Colloid Interface Sci. 351(2) (2010) 330-342.

J. C. Shillcock, Spontaneous vesicle self-assembly: a mesoscopic view of membrane dynamics, Langmuir 28(1) (2012) 541-7.

Y. Mai, A. Eisenberg, Self-assembly of block copolymers, Chem. Soc. Rev. 41(18) (2012) 5969-85.

R. S. Rikken, H. Engelkamp, R. J. Nolte, J. C. Maan, J. C. van Hest, D. A. Wilson, P. C. Christianen, Shaping polymersomes into predictable morphologies via out-of-equilibrium self-assembly, Nat Commun 7 (2016) 12606.

R. Salva, J. F. Le Meins, O. Sandre, A. Brulet, M. Schmutz, P. Guenoun, S. Lecommandoux, Polymersome shape transformation at the nanoscale, ACS Nano 7(10) (2013) 9298-311.

R. Lipowsky, The morphology of lipid membranes, Curr Opin Struct Biol 5(4) (1995) 531-40.

M. Dionzou, A. Morere, C. Roux, B. Lonetti, J. D. Marty, C. Mingotaud, P. Joseph, D. Goudouneche, B. Payre, M. Leonetti, A. F. Mingotaud, Comparison of methods for the fabrication and the characterization of polymer self-assemblies: what are the important parameters?, Soft Matter 12(7) (2016) 2166-76.

R. Bleul, R. Thiermann, M. Maskos, Techniques To Control Polymersome Size, Macromolecules 48(20) (2015) 7396-7409.

B. K. Johnson, R. K. Prud'homme, Mechanism for rapid self-assembly of block copolymer nanoparticles, Phys. Rev. Lett. 91(11) (2003) 118302.

V. Kumar, R. K. Prud'homme, Nanoparticle stability: Processing pathways for solvent removal, Chem. Eng. Sci. 64(6) (2009) 1358-1361.

V. Kumar, L. Wang, M. Riebe, H. H. Tung, R. K. Prud'homme, Formulation and stability of itraconazole and odanacatib nanoparticles: governing physical parameters, Mol Pharm 6(4) (2009) 1118-24.

J. F. Le Meins, O. Sandre, S. Lecommandoux, Recent trends in the tuning of polymersomes' membrane properties, Eur Phys J E Soft Matter 34(2) (2011) 14.

B. M. Discher, Y. Y. Won, D. S. Ege, J. C. Lee, F. S. Bates, D. E. Discher, D. A. Hammer, Polymersomes: tough vesicles made from diblock copolymers, Science 284 (5417) (1999) 1143-6.

S. Allen, Y. G. Liu, E. Scott, Engineering nanomaterials to address cell-mediated inflammation in atherosclerosis, Regen Eng Transl Med 2(1) (2016) 37-50.

A. E. Vasdekis, E. A. Scott, S. Roke, J. A. Hubbell, D. Psaltis, Vesicle Photonics, Annu. Rev. Mater. Res. 43 (2013) 283-305.

J. D. Robertson, G. Yealland, M. Avila-Olias, L. Chierico, O. Bandmann, S. A. Renshaw, G. Battaglia, pH-sensitive tubular polymersomes: formation and applications in cellular delivery, ACS Nano 8(5) (2014) 4650-61.

J. Cui, J. Xu, Y. Zhu, W. Jiang, Shear flow controlled morphological polydispersity of amphiphilic ABA triblock copolymer vesicles, Langmuir 29(50) (2013) 15704-10.

R. Thiermann, W. Mueller, A. Montesinos-Castellanos, D. Metzke, P. Lob, V. Hessel, M. Maskos, Size controlled polymersomes by continuous self-assembly in micromixers, Polymer 53(11) (2012) 2205-2210.

Y. La, C. Park, T. J. Shin, S. H. Joo, S. Kang, K. T. Kim, Colloidal inverse bicontinuous cubic membranes of block copolymers with tunable surface functional groups, Nat Chem 6(6) (2014) 534-41.

M. C. van Oers, F. P. Rutjes, J. C. van Hest, Tubular polymersomes: a cross-linker-induced shape transformation, J. Am. Chem. Soc. 135(44) (2013) 16308-11.

R. S. Rikken, H. H. Kerkenaar, R. J. Nolte, J. C. Maan, J. C. van Hest, P. C. Christianen, D. A. Wilson, Probing morphological changes in polymersomes with magnetic birefringence, Chem Commun (Camb) 50(40) (2014) 5394-6.

K. T. Kim, J. Zhu, S. A. Meeuwissen, J. J. Cornelissen, D. J. Pochan, R. J. Nolte, J. C. van Hest, Polymersome stomatocytes: controlled shape transformation in polymer vesicles, J. Am. Chem. Soc. 132(36) (2010) 12522-4.

P. L. Soo, A. Eisenberg, Preparation of block copolymer vesicles in solution, J Polym Sci Pol Phys 42(6) (2004) 923-938.

H. Yabu, Creation of Functional and Structured Polymer Particles by Self-Organized Precipitation (SORP), Bull. Chem. Soc. Jpn. 85(3) (2012) 265-274.

H. C. Shum, J. W. Kim, D. A. Weitz, Microfluidic fabrication of monodisperse biocompatible and biodegradable polymersomes with controlled permeability, J. Am. Chem. Soc. 130(29) (2008) 9543-9.

E. A. Scott, A. Stano, M. Gillard, A. C. Maio-Liu, M. A. Swartz, J. A. Hubbell, Dendritic cell activation and T cell priming with adjuvant- and antigen-loaded oxidation-sensitive polymersomes, Biomaterials 33(26) (2012) 6211-9.

D. A. Hammer, N. P. Kamat, Towards an artificial cell, FEBS Lett. 586(18) (2012) 2882-2890.

J. Pessi, H. A. Santos, I. Miroshnyk, J. Yliruusi, D. A. Weitz, S. Mirza, Microfluidics-assisted engineering of polymeric microcapsules with high encapsulation efficiency for protein drug delivery, Int. J. Pharm. 472(1-2) (2014) 82-87.

A. Napoli, M. Valentini, N. Tirelli, M. Muller, J. A. Hubbell, Oxidation-responsive polymeric vesicles, Nat. Mater. 3(3) (2004) 183-9.

E. Nicol, T. Nicolai, D. Durand, Dynamics of poly(propylene sulfide) studied by dynamic mechanical measurements and dielectric spectroscopy, Macromolecules 32(22) (1999) 7530-7536.

S. Cerritelli, C. P. O'Neil, D. Velluto, A. Fontana, M. Adrian, J. Dubochet, J. A. Hubbell, Aggregation Behavior of Poly(ethylene glycol-bl-propylene sulfide) Di- and Triblock Copolymers in Aqueous Solution, Langmuir 25(19) (2009) 11328-11335.

S. Cerritelli, A. Fontana, D. Velluto, M. Adrian, J. Dubochet, P. De Maria, J. A. Hubbell, Thermodynamic and kinetic effects in the aggregation behavior of a poly(ethylene glycol-b-propylene sulfide-b-ethylene glycol) ABA triblock copolymer, Macromolecules 38(18) (2005) 7845-7851.

A. E. Vasdekis, E. A. Scott, C. P. O'Neil, D. Psaltis, J. A. Hubbell, Precision intracellular delivery based on optofluidic polymersome rupture, ACS Nano 6(9) (2012) 7850-7.

T. Segura, J. A. Hubbell, Synthesis and in vitro characterization of an ABC triblock copolymer for siRNA delivery, Bioconjugate Chem. 18(3) (2007) 736-745.

C. P. O'Neil, T. Suzuki, D. Demurtas, A. Finka, J. A. Hubbell, A Novel Method for the Encapsulation of Biomolecules into Polymersomes via Direct Hydration, Langmuir 25(16) (2009) 9025-9029.

M. Akbulut, P. Ginart, M. E. Gindy, C. Theriault, K. H. Chin, W. Soboyejo, R. K. Prud'homme, Generic Method of Preparing Multifunctional Fluorescent Nanoparticles Using Flash NanoPrecipitation, Adv. Funct. Mater. 19(5) (2009) 718-725.

A. R. Wohl, A. R. Michel, S. Kalscheuer, C. W. Macosko, J. Panyam, T. R. Hoye, Silicate esters of paclitaxel and docetaxel: synthesis, hydrophobicity, hydrolytic stability, cytotoxicity, and prodrug potential, J. Med. Chem. 57(6) (2014) 2368-79.

Z. Zhu, Flash nanoprecipitation: prediction and enhancement of particle stability via drug structure, Mol Pharm 11(3) (2014) 776-86.

M. D. Nichols, E. A. Scott, D. L. Elbert, Factors affecting size and swelling of poly(ethylene glycol) microspheres formed in aqueous sodium sulfate solutions without surfactants, Biomaterials 30(29) (2009) 5283-91.

E. A. Scott, M. D. Nichols, R. Kuntz-Willits, D. L. Elbert, Modular scaffolds assembled around living cells using poly(ethylene glycol) microspheres with macroporation via a non-cytotoxic porogen, Acta Biomater 6(1) (2010) 29-38.

B. E. McKenzie, J. F. de Visser, H. Friedrich, M. J. M. Wirix, P. H. H. Bomans, G. de With, S. J. Holder, N. A. J. M. Sommerdijk, Bicontinuous Nanospheres from Simple Amorphous Amphiphilic Diblock Copolymers, Macromolecules 46(24) (2013) 9845-9848.

T. I. Lobling, O. Borisov, J. S. Haataja, O. Ikkala, A. H. Groschel, A. H. Muller, Rational design of ABC triblock terpolymer solution nanostructures with controlled patch morphology, Nat Commun 7 (2016) 12097.

N. Saito, C. Liu, T. P. Lodge, M. A. Hillmyer, Multicompartment Micelles from Polyester-Containing ABC Miktoarm Star Terpolymers, Macromolecules 41(22) (2008) 8815-8822.

S. I. Jeon, J. H. Lee, J. D. Andrade, P. G. Degennes, Protein Surface Interactions in the Presence of Polyethylene Oxide 0.1. Simplified Theory, J. Colloid Interface Sci. 142(1) (1991) 149-158.

S. Stewart, G. Liu, Block Copolymer Nanotubes, Angew. Chem. Int. Ed. Engl. 39(2) (2000) 340-344.

J. Grumelard, A. Taubert, W. Meier, Soft nanotubes from amphiphilic ABA triblock macromonomers, Chem Commun (Camb) (13) (2004) 1462-3.

M. Massignani, I. Canton, T. Sun, V. Hearnden, S. Macneil, A. Blanazs, S. P. Armes, A. Lewis, G. Battaglia, Enhanced fluorescence imaging of live cells by effective cytosolic delivery of probes, PLoS One 5(5) (2010) e10459.

K. M. Pustulka, A. R. Wohl, H. S. Lee, A. R. Michel, J. Han, T. R. Hoye, A. V. McCormick, J. Panyam, C. W. Macosko, Flash nanoprecipitation: particle structure and stability, Mol Pharm 10(11) (2013) 4367-77.

N. M. Pinkerton, A. Grandeury, A. Fisch, J. Brozio, B. U. Riebesehl, R. K. Prud'homme, Formation of stable nanocarriers by in situ ion pairing during block-copolymer-directed rapid precipitation, Mol Pharm 10(1) (2013) 319-28.

B. Maherani, E. Arab-Tehrany, A. Kheirolomoom, D. Geny, M. Linder, Calcein release behavior from liposomal bilayer; influence of physicochemical/mechanical/structural properties of lipids, Biochimie 95(11) (2013) 2018-33.

J. P. Horwitz, J. Chua, M. Noel, J. T. Donatti, J. Freisler, Substrates for cytochemical demonstration of enzyme activity. II. Some dihalo-3-indolyl phosphates and sulfates, J. Med. Chem. 9(3) (1966) 447.

J. J. Coenen, H. J. Koenen, E. van Rijssen, A. Kasran, L. Boon, L. B. Hilbrands, I. Joosten, Rapamycin, not cyclosporine, permits thymic generation and peripheral preservation of CD4+ CD25+ FoxP3+ T cells, Bone Marrow Transplant 39(9) (2007) 537-45.

M. Noris, F. Casiraghi, M. Todeschini, P. Cravedi, D. Cugini, G. Monteferrante, S. Aiello, L. Cassis, E. Gotti, F. Gaspari, D. Cattaneo, N. Perico, G. Remuzzi, Regulatory T cells and T cell depletion: role of immunosuppressive drugs, J Am Soc Nephrol 18(3) (2007) 1007-18.

W. Cao, S. Manicassamy, H. Tang, S. P. Kasturi, A. Pirani, N. Murthy, B. Pulendran, Toll-like receptor-mediated induction of type I interferon in plasmacytoid dendritic cells requires the rapamycin-sensitive PI(3)K-mTOR-p70S6K pathway, Nat Immunol 9(10) (2008) 1157-64.

A. W. Thomson, H. R. Turnquist, G. Raimondi, Immunoregulatory functions of mTOR inhibition, Nat Rev Immunol 9(5) (2009) 324-37.

H. R. Turnquist, G. Raimondi, A. F. Zahorchak, R. T. Fischer, Z. Wang, A. W. Thomson, Rapamycin-conditioned dendritic cells are poor stimulators of allogeneic CD4+ T cells, but enrich for antigen-specific Foxp3+ T regulatory cells and promote organ transplant tolerance, J Immunol 178(11) (2007) 7018-31.

A. Haddadi, P. Elamanchili, A. Lavasanifar, S. Das, J. Shapiro, J. Samuel, Delivery of rapamycin by PLGA nanoparticles enhances its suppressive activity on dendritic cells, J Biomed Mater Res A 84(4) (2008) 885-98.

S. Jhunjhunwala, G. Raimondi, A. W. Thomson, S. R. Little, Delivery of rapamycin to dendritic cells using degradable microparticles, J Control Release 133(3) (2009) 191-7.

A. Mercalli, I. Calavita, E. Dugnani, A. Citro, E. Cantarelli, R. Nano, R. Melzi, P. Maffi, A. Secchi, V. Sordi, L. Piemonti, Rapamycin unbalances the polarization of human macrophages to M1, Immunology 140(2) (2013) 179-90.

S. Yi, S. D. Allen, Y. G. Liu, B. Z. Ouyang, X. Li, P. Augsornworawat, E. B. Thorp, E. A. Scott, Tailoring Nanostructure Morphology for Enhanced Targeting of Dendritic Cells in Atherosclerosis, ACS Nano 10(12) (2016) 11290-11303.

D. J. Dowling, E. A. Scott, A. Scheid, I. Bergelson, D. I. Kats, G. Sanchez-Schmitz, S. D. Van Haren, J. Ninkovic, D. K. Bonner, S. Hirosue, J. A. Hubbell, O. Levy, TLR8 agonist encapsulating polymersomes mimic the immunomodulating effect of the live BCG vaccine on neonatal dendritic cells while dramatically enhancing IL-12p70 production, Journal of Clinical Investigation In Press (2017).

X. Li, K. Garcia, Z. Sun, Z. Xiao, Temporal regulation of rapamycin on memory CTL programming by IL-12, PloS one 6(9) (2011) e25177.

X. L. Liu, L. Luo, R. H. Mu, B. B. Liu, D. Geng, Q. Liu, L. T. Yi, Fluoxetine regulates mTOR signalling in a region-dependent manner in depression-like mice, Scientific reports 5 (2015) 16024.

L. Stoica, P. J. Zhu, W. Huang, H. Zhou, S. C. Kozma, M. Costa-Mattioli, Selective pharmacogenetic inhibition of mammalian target of Rapamycin complex I (mTORC1) blocks long-term synaptic plasticity and memory storage, Proceedings of the National Academy of Sciences of the United States of America 108(9) (2011) 3791-6.

T. S. Ikonen, J. F. Gummert, N. Serkova, M. Hayase, Y. Honda, Y. Kobayase, B. Hausen, P. G. Yock, U. Christians, R. E. Morris, Efficacies of sirolimus (rapamycin) and cyclosporine in allograft vascular disease in non-human primates: trough levels of sirolimus correlate with inhibition of progression of arterial intimal thickening, Transpl Int 13 Suppl 1 (2000) S314-20.

A. Xiong, L. Duan, J. Chen, Z. Fan, F. Zheng, Z. Tan, F. Gong, M. Fang, Flt3L combined with rapamycin promotes cardiac allograft tolerance by inducing regulatory dendritic cells and allograft autophagy in mice, PloS one 7(10) (2012) e46230.

R. S. Poston, M. Billingham, E. G. Hoyt, J. Pollard, R. Shorthouse, R. E. Morris, R. C. Robbins, Rapamycin reverses chronic graft vascular disease in a novel cardiac allograft model, Circulation 100(1) (1999) 67-74.

M. Battaglia, A. Stabilini, M. G. Roncarolo, Rapamycin selectively expands CD4+CD25+FoxP3+ regulatory T cells, Blood 105(12) (2005) 4743-8.

Y. Qu, B. Zhang, L. Zhao, G. Liu, H. Ma, E. Rao, C. Zeng, Y. Zhao, The effect of immunosuppressive drug rapamycin on regulatory CD4+CD25+Foxp3+T cells in mice, Transpl Immunol 17(3) (2007) 153-61.

W. Gao, Y. Lu, B. El Essawy, M. Oukka, V. K. Kuchroo, T. B. Strom, Contrasting effects of cyclosporine and rapamycin in de novo generation of alloantigen-specific regulatory T cells, Am J Transplant 7(7) (2007) 1722-32.

T. Sterling, J. J. Irwin, ZINC 15—Ligand Discovery for Everyone, J Chem Inf Model 55(11) (2015) 2324-37.

M. B. Lutz, N. Kukutsch, A. L. Ogilvie, S. Rossner, F. Koch, N. Romani, G. Schuler, An advanced culture method for generating large quantities of highly pure dendritic cells from mouse bone marrow, J Immunol Methods 223(1) (1999) 77-92.

We claim:

1. A method for preparing aqueous-core nanocarriers by flash precipitation comprising the steps of:
   (i) providing an organic phase solution comprising poly (ethylene glycol)-bl-poly(propylene sulfide) (PEG-bl-PPS) and a process solvent, wherein the PEG-bl-PPS has a glass transition temperature below 0° C.,
   (ii) providing an aqueous phase solution comprising an aqueous solvent,
   (iii) mixing the organic phase solution and the aqueous phase solution by impingement to form a mixture, and
   (iv) introducing the mixture into a reservoir to cause precipitation of the PEG-bl-PPS as an aqueous-core nanocarrier.

2. The method of claim 1, wherein the process solvent is selected from the group consisting of tetrahydrofuran (THF), dimethylformamide (DMF), and dimethyl sulfoxide (DMSO).

3. The method of claim 1, wherein the aqueous solvent is water.

4. The method of claim 1, wherein the PEG-bl-PPS has a glass transition temperature between about −40° C. and about 0° C.

5. The method of claim 1, wherein the PEG-bl-PPS is PEG17-bl-PPS$_{30}$-Thiol.

6. The method of claim 1, wherein the organic phase solution additionally comprises one or more target molecules.

7. The method of claim 1, wherein the aqueous phase solution additionally comprises a target molecule.

8. The method of claim 7, wherein the target molecule is selected from the group consisting of a DNA molecule, an RNA molecule, a plasmid, a peptide, a protein, and combinations thereof.

9. The method of claim 1, wherein the reservoir comprises an aqueous nonsolvent.

10. The method of claim 1, wherein the reservoir comprises a target molecule.

11. The method of claim 1, wherein the mixing comprises at least 2 impingements.

12. A method for preparing aqueous-core nanocarriers by flash precipitation comprising the steps of:
   (i) providing an organic phase solution comprising poly (ethylene glycol)-bl-poly(propylene sulfide) (PEG-bl-PPS) and a process solvent, wherein the PEG-bl-PPS has a glass transition temperature below 0° C.,
   (ii) providing an aqueous phase solution comprising an aqueous solvent and an target molecule,
   (iii) mixing the organic phase solution and the aqueous phase solution by impingement to form a mixture, and
   (iv) introducing the mixture into a reservoir to cause precipitation of the PEG-bl-PPS as an aqueous-core nanocarrier loaded with the target molecule.

13. The method of claim 12, wherein the target molecule is selected from the group consisting of a DNA molecule, an RNA molecule, a plasmid, a peptide, a protein, and combinations thereof.

14. The method of claim 12, wherein the process solvent is selected from the group consisting of tetrahydrofuran (THF), dimethylformamide (DMF), and dimethyl sulfoxide (DMSO).

15. The method of claim 12, wherein the aqueous solvent is water.

16. The method of claim 12, wherein the PEG-bl-PPS has a glass transition temperature between about −40° C. and about 0° C.

17. The method of claim 12, wherein the PEG-bl-PPS is PEG$_{17}$-bl-PPS$_{30}$-Thiol.

18. The method of claim 12, wherein the organic phase solution additionally comprises a target molecule.

19. A method for preparing aqueous-core nanocarriers by flash precipitation comprising the steps of:
   (i) providing an organic phase solution comprising poly (ethylene glycol)-bl-poly(propylene sulfide) (PEG-bl-PPS) and a process solvent, wherein the PEG-bl-PPS has a glass transition temperature below 0° C.,
   (ii) providing an aqueous phase solution comprising an aqueous solvent and an target molecule,
   (iii) mixing the organic phase solution and the first aqueous phase solution to form a mixture,
   (iii) portioning the mixture into a first portion and a second portion,
   (iv) mixing the first portion and the second portion by impingement to form a second mixture, and
   (v) introducing the second mixture into a reservoir to cause precipitation of the PEG-bl-PPS as an aqueous-core nanocarrier loaded with the target molecule.

20. The method of claim 19, wherein steps (iii) and (iv) are repeated at least one time.

21. The method of claim 19, wherein the organic phase solution additionally comprises a second target molecule.

22. The method of claim 1, wherein the aqueous-core nanocarrier is selected from the group consisting of tubular polymersomes, bicontinuous nanospheres, polymersomes, and multilamellar polymersomes.

23. The method of claim 12, wherein the aqueous-core nanocarrier is selected from the group consisting of tubular polymersomes, bicontinuous nanospheres, polymersomes, and multilamellar polymersomes.

24. The method of claim 19, wherein the aqueous-core nanocarrier is selected from the group consisting of tubular polymersomes, bicontinuous nanospheres, polymersomes, and multilamellar polymersomes.

* * * * *